(12) United States Patent
Jasemian et al.

(10) Patent No.: US 10,905,420 B2
(45) Date of Patent: Feb. 2, 2021

(54) RELOAD SHAFT ASSEMBLY FOR SURGICAL STAPLER

(71) Applicant: Applied Medical Resources Corporation, Rancho Santa Margarita, CA (US)

(72) Inventors: Babak D. Jasemian, Trabuco Canyon, CA (US); Steven E. Decker, Anaheim, CA (US); Atal C. Patel, Mission Viejo, CA (US); Erik Nelson, Rancho Santa Margarita, CA (US); Andrew J. McCarthy, Trabuco Canyon, CA (US); Scott Zimmerman, Lancaster, CA (US); Timothy M. Hopkins, Rancho Santa Margarita, CA (US); Joshua M. Schober, Temecula, CA (US); Eric J. Weiss, Rancho Santa Margarita, CA (US); Matthew M. Becerra, Lake Forest, CA (US); Christina N. Reed, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 433 days.

(21) Appl. No.: 15/486,227

(22) Filed: Apr. 12, 2017

(65) Prior Publication Data

US 2017/0290584 A1 Oct. 12, 2017

Related U.S. Application Data

(60) Provisional application No. 62/321,618, filed on Apr. 12, 2016.

(51) Int. Cl.
*A61B 17/072* (2006.01)
*A61B 90/00* (2016.01)
(Continued)

(52) U.S. Cl.
CPC ...... *A61B 17/07207* (2013.01); *A61B 17/072* (2013.01); *A61B 90/90* (2016.02);
(Continued)

(58) Field of Classification Search
CPC .......... A61B 2017/07271; A61B 2017/07278; A61B 2017/07285
See application file for complete search history.

(56) References Cited

U.S. PATENT DOCUMENTS

| | | | |
|---|---|---|---|
| 2,073,960 A | 3/1937 | Crosby | |
| 2,140,593 A | 12/1938 | Pankonin | |

(Continued)

FOREIGN PATENT DOCUMENTS

| | | | |
|---|---|---|---|
| EP | 0 251 444 A1 | 1/1988 | |
| EP | 0 492 283 A1 | 7/1992 | |

(Continued)

OTHER PUBLICATIONS

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

(Continued)

*Primary Examiner* — Stephen F. Gerrity
*Assistant Examiner* — Joshua G Kotis
(74) *Attorney, Agent, or Firm* — John F. Heal

(57) ABSTRACT

A surgical stapling system can include a reload shaft. The shaft can include an elongate tubular member with have a jaw assembly at the distal end thereof and a coupling collar at the proximal end thereof. The shaft assembly also includes an articulation joint coupling the jaw assembly to the distal end. A drive member and an articulation member extend within the tubular body of the shaft from the proximal end to the distal end. A firing member is connected to (Continued)

the distal end of the drive member such that advancement of the drive beam advances the firing member to close the jaw assemblies and fire staples from a reload positioned in the jaw assembly. The shaft assembly can also include a lockout mechanism to prevent a firing operation on a previously-fired reload or no reload.

10 Claims, 26 Drawing Sheets

(51) Int. Cl.
  A61B 17/29 (2006.01)
  A61B 17/00 (2006.01)
  A61B 90/90 (2016.01)
(52) U.S. Cl.
  CPC ............. *A61B 2017/0046* (2013.01); *A61B 2017/00477* (2013.01); *A61B 2017/00526* (2013.01); *A61B 2017/07257* (2013.01); *A61B 2017/07264* (2013.01); *A61B 2017/07278* (2013.01); *A61B 2017/07285* (2013.01); *A61B 2017/2927* (2013.01); *A61B 2090/038* (2016.02); *A61B 2090/0808* (2016.02); *A61B 2090/0814* (2016.02)

(56) References Cited

U.S. PATENT DOCUMENTS

| | | | |
|---|---|---|---|
| 2,351,608 A | 6/1944 | Greenwood | |
| 2,487,565 A | 11/1949 | Leber et al. | |
| 2,641,154 A | 6/1953 | Heller | |
| 3,076,373 A | 2/1963 | Matthews | |
| 3,077,812 A | 2/1963 | Dietrich | |
| 3,080,564 A | 3/1963 | Strekopitov et al. | |
| 3,203,220 A | 8/1965 | Kaepernik | |
| 3,252,643 A | 5/1966 | Strekopitov et al. | |
| 3,273,562 A | 9/1966 | Brown | |
| 3,373,646 A | 3/1968 | Ehlert | |
| 3,459,187 A | 8/1969 | Pallotta | |
| 3,494,533 A | 2/1970 | Green et al. | |
| 3,662,939 A | 5/1972 | Bryan | |
| 3,675,688 A | 7/1972 | Bryan et al. | |
| 3,692,224 A | 9/1972 | Astafiev et al. | |
| 4,261,244 A | 4/1981 | Becht et al. | |
| 4,281,785 A | 8/1981 | Brooks | |
| 4,304,236 A | 12/1981 | Conta et al. | |
| 4,312,363 A | 1/1982 | Rothfuss et al. | |
| 4,317,451 A | 3/1982 | Cerwin et al. | |
| 4,407,286 A | 10/1983 | Noiles et al. | |
| 4,434,796 A | 3/1984 | Karapetian et al. | |
| 4,442,964 A | 4/1984 | Becht | |
| 4,454,875 A | 6/1984 | Pratt et al. | |
| 4,522,327 A | 6/1985 | Korthoff et al. | |
| 4,527,724 A | 7/1985 | Chow et al. | |
| 4,589,582 A | 5/1986 | Bilotti | |
| 4,591,085 A | 5/1986 | Di Giovanni | |
| 4,606,344 A | 8/1986 | Di Giovanni | |
| 4,608,981 A | 9/1986 | Rothfuss et al. | |
| 4,610,383 A | 9/1986 | Rothfuss et al. | |
| 4,728,020 A | 3/1988 | Green et al. | |
| 4,805,823 A | 2/1989 | Rothfuss | |
| 4,892,244 A | 1/1990 | Fox et al. | |
| 4,923,350 A | 5/1990 | Hinksman et al. | |
| 4,941,623 A | 7/1990 | Pruitt | |
| 4,955,959 A | 9/1990 | Tompkins et al. | |
| 4,978,049 A | 12/1990 | Green | |
| 5,031,814 A * | 7/1991 | Tompkins ........ | A61B 17/07207 227/1 |
| 5,065,929 A | 11/1991 | Schulze et al. | |
| 5,071,052 A | 12/1991 | Rodak et al. | |
| 5,106,008 A | 4/1992 | Tompkins et al. | |
| 5,116,349 A | 5/1992 | Aranyi | |
| 5,129,570 A | 7/1992 | Schulze et al. | |
| 5,201,746 A | 4/1993 | Shichman | |
| 5,221,036 A | 6/1993 | Takase | |
| 5,236,440 A | 8/1993 | Hlavacek | |
| 5,240,163 A | 8/1993 | Stein et al. | |
| RE34,519 E | 1/1994 | Fox et al. | |
| 5,275,323 A | 1/1994 | Schulze et al. | |
| 5,289,963 A | 3/1994 | McGarry et al. | |
| D347,474 S | 5/1994 | Olson | |
| 5,307,976 A | 5/1994 | Olson et al. | |
| 5,308,576 A | 5/1994 | Green et al. | |
| 5,326,013 A | 7/1994 | Green et al. | |
| 5,350,400 A | 9/1994 | Esposito et al. | |
| 5,360,305 A | 11/1994 | Kerrigan | |
| 5,364,002 A | 11/1994 | Green et al. | |
| 5,366,479 A | 11/1994 | McGarry et al. | |
| 5,381,943 A | 1/1995 | Allen et al. | |
| 5,389,098 A | 2/1995 | Tsuruta et al. | |
| 5,395,034 A | 3/1995 | Allen et al. | |
| 5,397,046 A | 3/1995 | Savage et al. | |
| 5,413,267 A | 5/1995 | Solyntjes et al. | |
| 5,415,334 A | 5/1995 | Williamson, IV et al. | |
| 5,415,335 A | 5/1995 | Knodell, Jr. | |
| 5,439,155 A | 8/1995 | Viola | |
| 5,439,479 A | 8/1995 | Shichman et al. | |
| 5,445,304 A | 8/1995 | Plyley et al. | |
| 5,447,265 A | 9/1995 | Vidal et al. | |
| 5,452,836 A | 9/1995 | Huitema et al. | |
| 5,456,401 A | 10/1995 | Green et al. | |
| 5,458,279 A | 10/1995 | Plyley | |
| 5,462,215 A | 10/1995 | Viola et al. | |
| 5,464,144 A | 11/1995 | Guy et al. | |
| 5,465,895 A * | 11/1995 | Knodel ............ | A61B 17/07207 227/176.1 |
| 5,470,006 A | 11/1995 | Rodak | |
| 5,470,007 A | 11/1995 | Plyley et al. | |
| 5,470,008 A | 11/1995 | Rodak | |
| 5,470,009 A | 11/1995 | Rodak | |
| 5,472,132 A | 12/1995 | Savage et al. | |
| 5,480,089 A | 1/1996 | Blewett | |
| 5,485,952 A | 1/1996 | Fontayne | |
| 5,487,500 A | 1/1996 | Knodel et al. | |
| 5,489,058 A | 2/1996 | Plyley | |
| 5,497,933 A | 3/1996 | DeFonzo et al. | |
| 5,507,426 A | 4/1996 | Young et al. | |
| 5,507,773 A | 4/1996 | Huitema et al. | |
| 5,509,596 A | 4/1996 | Green et al. | |
| 5,509,920 A | 4/1996 | Phillips et al. | |
| 5,529,235 A | 6/1996 | Boiarski et al. | |
| 5,547,117 A | 8/1996 | Hamblin et al. | |
| 5,553,765 A | 9/1996 | Knodel et al. | |
| 5,554,164 A | 9/1996 | Wilson et al. | |
| 5,558,266 A | 9/1996 | Green et al. | |
| 5,562,241 A | 10/1996 | Knodel et al. | |
| 5,562,700 A | 10/1996 | Huitema et al. | |
| 5,562,701 A | 10/1996 | Huitema et al. | |
| 5,562,702 A | 10/1996 | Huitema et al. | |
| 5,564,615 A | 10/1996 | Bishop et al. | |
| 5,571,285 A | 11/1996 | Chow et al. | |
| 5,579,978 A | 12/1996 | Green et al. | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,607,095 A | 3/1997 | Smith et al. | |
| 5,615,820 A | 4/1997 | Viola | |
| 5,626,587 A | 5/1997 | Bishop et al. | |
| 5,630,539 A | 5/1997 | Plyley et al. | |
| 5,634,584 A | 6/1997 | Okorocha et al. | |
| 5,636,779 A | 6/1997 | Palmer | |
| 5,657,921 A | 8/1997 | Young et al. | |
| 5,662,258 A | 9/1997 | Knodel et al. | |
| 5,662,662 A | 9/1997 | Bishop et al. | |
| 5,662,667 A | 9/1997 | Knodel | |
| 5,673,840 A | 10/1997 | Schulze et al. | |
| 5,673,841 A | 10/1997 | Schulze et al. | |
| 5,673,842 A | 10/1997 | Bittner et al. | |

(56) References Cited

U.S. PATENT DOCUMENTS

| | | |
|---|---|---|
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |

(56) References Cited

U.S. PATENT DOCUMENTS

| | | |
|---|---|---|
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |

(56) References Cited

U.S. PATENT DOCUMENTS

| | | |
|---|---|---|
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 10,245,036 B1 * | 4/2019 | Schaller ............ A61B 17/07207 |
| 2002/0025243 A1 | 2/2002 | Heck |

(56) References Cited

U.S. PATENT DOCUMENTS

| | | |
|---|---|---|
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2004/0232200 A1* | 11/2004 | Shelton, IV ..... A61B 17/07207 227/176.1 |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0102475 A1* | 5/2007 | Ortiz ................ A61B 17/07207 227/175.2 |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0065604 A1* | 3/2010 | Weng ................ A61B 17/07207 227/175.2 |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0301095 A1* | 12/2010 | Shelton, IV ............ A61B 17/00 227/175.4 |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Baxter, III et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327808 A1* | 12/2013 | Chen ................ A61B 17/07207 227/175.2 |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0058388 A1* | 2/2014 | Weisshaupt ........ A61B 18/1445 606/52 |
| 2014/0103092 A1 | 4/2014 | Kostrzewski et al. |
| 2014/0103093 A1 | 4/2014 | Koch, Jr. et al. |

(56) References Cited

U.S. PATENT DOCUMENTS

| | | |
|---|---|---|
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1* | 9/2014 | Aranyi ............ A61B 17/07207 227/175.3 |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0265275 A1* | 9/2015 | Chen ................ A61B 17/07207 227/175.3 |
| 2015/0272576 A1* | 10/2015 | Cappola ........... A61B 17/07207 227/175.2 |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2015/0316431 A1* | 11/2015 | Collins ............. A61B 17/07207 606/219 |
| 2015/0374363 A1* | 12/2015 | Laurent, IV ......... A61B 17/068 227/175.3 |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0157863 A1* | 6/2016 | Williams ............ A61B 17/068 227/175.2 |
| 2016/0183948 A1 | 6/2016 | Shelton, IV et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |
| 2017/0296190 A1* | 10/2017 | Aronhalt ........... A61B 17/07207 |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |

(56) References Cited

FOREIGN PATENT DOCUMENTS

| | | |
|---|---|---|
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

OTHER PUBLICATIONS

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.

European Patent Office, The International Search Report and the Written Opinion of the International Searching Authority for International Application No. PCT/US2017/027213, entitled "Surgical Stapler Having a Powered Handle," dated Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.

Ethicon Endo Surgery, Inc., Contour Curved Cutter Stapler, 2014, 2 pgs.

Justright Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

European Patent Office, European Search Report for European Application No. EP 14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.

The International Bureau of WIPO, International Preliminary Report on Patentability, for International Application No. PCT/US2016/045993, entitled "Surgical Stapler Having Locking Articulation Joint," dated Feb. 15, 2018, 13 pgs.

European Patent Office, European Search Report for European Application No. 07784007.2, entitled "Surgical Stapler," dated Jun. 15, 2012, 6 pgs.

International Searching Authority, U.S., The International Search Report and the Written Opinion of the International Searching authority for international application PCT/US2014/027768, titled "Surgical Stapler with Expandable Jaw", dated Jul. 25, 2014, 17 pgs.

European Patent Office, International Search Report and Written Opinion for International Application No. PCT/US2014/028211, entitled "Surgical Stapler with Partial Pockets," dated Sep. 8, 2014, 17 pgs.

International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentability, for International Application No. PCT/US2015/035379, entitled "Surgical Stapler with Circumferential Firing," dated Dec. 22, 2016, 14 pgs.

The International Bureau of WIPO, International Preliminary Report on Patentability for International Application No. PCT/US2015/050103, titled "Surgical Stapler With Self-Adjusting Staple Height," dated Mar. 30, 2017, 12 pgs.

European Patent Office, Partial European Search Report for European Application No. EP 14762896.0, entitled "Surgical Stapler with Expandable Jaw," dated Apr. 10, 2017, 6 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability, for International Application No. PCT/US2017/027269, entitled "Reload Shaft Assembly for Surgical Stapler," dated Oct. 25, 2018, 12 pgs.

European Patent Office, Extended European Search Report for European Application No. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," dated Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees for PCTUS2020/025496, entitled "Reload Cover for Surgical Stapling System," dated Jun. 18, 2019, 15 pgs.

(56) References Cited

OTHER PUBLICATIONS

European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.

* cited by examiner

RELOAD SHAFT ASSEMBLY FOR SURGICAL STAPLER

CROSS REFERENCE TO RELATED APPLICATION

This application claims the benefit of U.S. Provisional Patent Application Ser. No. 62/321,618, entitled "RELOAD SHAFT ASSEMBLY FOR SURGICAL STAPLER," filed Apr. 12, 2016. The above-referenced application is incorporated by reference herein in its entirety.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a jaw assembly, and a handle assembly. The elongate shaft has a proximal end and a distal end. The elongate shaft defines a longitudinal axis between the proximal end and the distal end. The jaw assembly is positioned at the distal end of the elongate shaft. The jaw assembly comprises a first jaw, a second jaw, and a plurality of staples. The jaw assembly is selectively positionable in one of a closed configuration, an open configuration, and a firing configuration. The handle assembly is positioned at the proximal end of the elongate shaft.

In certain embodiments, the elongate shaft comprises a jaw assembly at the distal end thereof coupled at an articulation joint. The articulation joint can allow articulation of the jaw assembly about an articulation range. Translation of an articulation member that extends through the elongate shaft articulates the jaw assembly. The elongate shaft further comprises a drive member extending through the elongate shaft. The drive member has a flexible segment extending through the articulation joint. A firing member is coupled to the distal end of the drive member.

In certain embodiments, the jaw assembly at the distal end of the elongate shaft comprises a reload support and an anvil pivotably coupled to the reload support. A firing member having an I-beam configuration is positioned in the jaw assembly. The jaw assembly can further comprise a lockout mechanism to prevent the firing member from being advanced unless an unfired reload is positioned in the jaw assembly.

In various embodiments, a shaft coupler can be positioned at the proximal end of the shaft. The shaft coupler can be configured to engage a coupler on a handle assembly in a bayonet connection. The bayonet connection simultaneously couples an articulation member, a drive member, and the elongate shaft. The coupler can further comprise a shaft identification mechanism. The coupler can further comprise a lock-in mechanism to retain the shaft assembly in connection with the handle assembly.

In various embodiments, a reload assembly for a surgical stapling system is provided. The reload assembly comprises an elongate shaft, a jaw assembly, a firing member, an actuation beam, and a reload lockout mechanism. The elongate shaft has a proximal end and a distal end. The elongate shaft defines a longitudinal axis extending between the proximal end and the distal end. The jaw assembly is positioned at the distal end of the elongate shaft. The jaw assembly comprises a first jaw, and a second jaw. The first jaw comprises a reload support configured to receive a staple reload. The second jaw is pivotably coupled to the first jaw. The second jaw comprises an anvil surface. The firing member is longitudinally slidable within the jaw assembly. The actuation beam is longitudinally slidable within the elongate shaft. The actuation beam has a proximal end and a distal end. The distal end of the actuation beam is coupled to the firing member. The reload lockout mechanism comprises a lockout lever pivotally coupled to the reload support and pivotable between a locked position preventing distal movement of the actuation beam relative to the elongate shaft and an unlocked position allowing distal movement of the actuation beam relative to the elongate shaft.

In various embodiments, a reload assembly for a surgical stapling system is provided. The reload assembly comprises an elongate shaft, a jaw assembly, an actuation beam, and a shaft coupler. The elongate shaft has a proximal end and a distal end and defines a longitudinal axis extending between the proximal end and the distal end. The jaw assembly is positioned at the distal end of the elongate shaft. The jaw assembly comprises a first jaw, and a second jaw. The first jaw comprises a reload support configured to receive a staple reload. The second jaw is pivotably coupled to the first jaw. The second jaw comprises an anvil surface. The actuation beam is longitudinally slidable within the elongate shaft. The actuation beam has a proximal end and a distal end. The distal end of the actuation beam is coupled to the jaw assembly. The shaft coupler is positioned at the proximal end of the elongate shaft. The shaft coupler comprises a locking member positioned therein. The locking member is radially outwardly advanceable by distal actuation of the proximal end of the actuation beam.

In various embodiments, a reload assembly for a surgical stapling system is provided. The reload assembly comprises an elongate shaft, a jaw assembly, an actuation beam, and a shaft coupler. The elongate shaft has a proximal end and a distal end and defines a longitudinal axis extending between the proximal end and the distal end. The jaw assembly is positioned at the distal end of the elongate shaft. The jaw assembly comprises a first jaw and a second jaw. The first jaw comprises a reload support configured to receive a staple reload. The second jaw is pivotably coupled to the first jaw. The second jaw comprises an anvil surface. The actuation beam is longitudinally slidable within the elongate shaft. The actuation beam has a proximal end and a distal end. The distal end of the actuation beam is coupled to the jaw assembly. The shaft coupler is positioned at the proximal end of the elongate shaft. The shaft coupler is configured to removably couple to a handle assembly. The shaft coupler comprises a lockout mechanism positioned therein. The lockout mechanism comprises a locking ring and a lockout member. The locking ring is rotatable about the longitudinal axis. The lockout member is radially outwardly advanceable by rotation of the locking ring.

In various embodiments, a reload assembly for a surgical stapling system is provided. The reload assembly comprises an elongate shaft, a jaw assembly, an actuation beam, an articulation link, a support link, and an articulation latching mechanism. The elongate shaft has a proximal end and a distal end and defines a longitudinal axis extending between the proximal end and the distal end. The jaw assembly is articulably coupled to the elongate shaft at the distal end of the elongate shaft. The jaw assembly comprises a first jaw and a second jaw. The first jaw comprises a reload support configured to receive a staple reload. The second jaw is pivotably coupled to the first jaw. The second jaw comprises an anvil surface. The actuation beam is longitudinally slidable within the elongate shaft to actuate the jaw assembly. The actuation beam has a proximal end and a distal end. The articulation link is longitudinally slidable within the elongate shaft to articulate the jaw assembly relative to the elongate shaft. The articulation link has a proximal end positioned adjacent the proximal end of the elongate shaft and a distal end pivotably coupled to the jaw assembly. The support link is longitudinally slidable within the elongate shaft. The support link has a proximal end extending longitudinally to a distal end pivotably coupled to the jaw assembly. The articulation latching mechanism is positioned within the elongate shaft between the proximal end and the distal end. The articulation latching mechanism has an unlatched configuration in which the articulation link and the support link are slidable within the elongate shaft and a latched configuration wherein the articulation latching mechanism engages the articulation link and the support link to prevent longitudinal sliding of the articulation link and the support link.

DETAILED DESCRIPTION OF THE INVENTION

Figure 1:
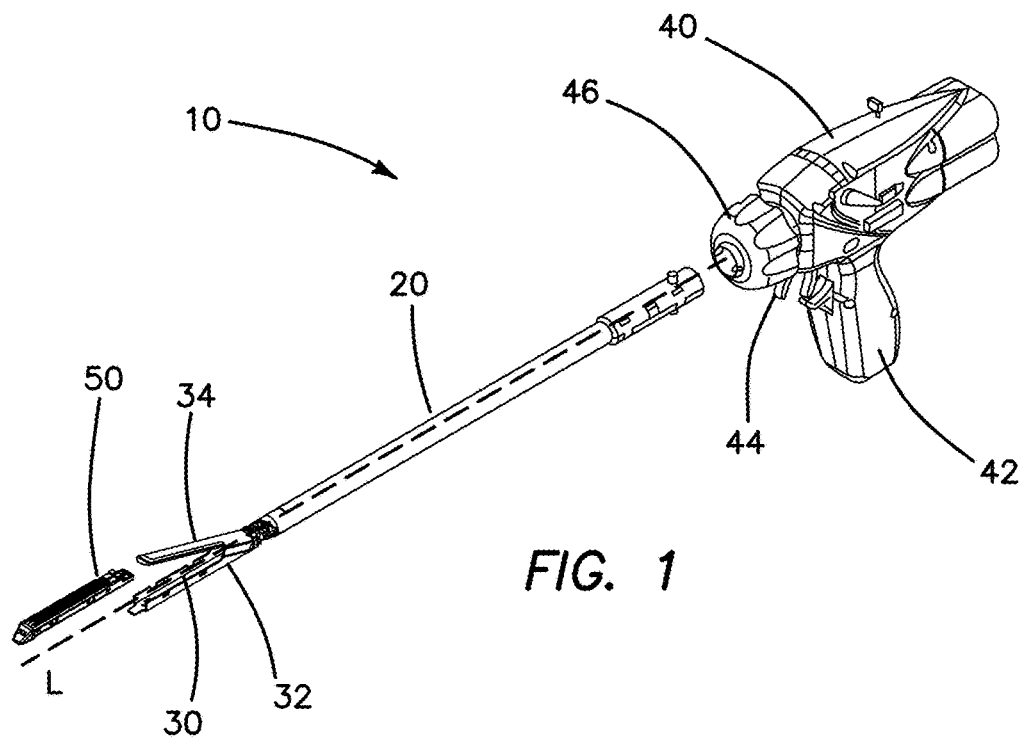
FIG. 1 is a perspective view of an embodiment of surgical stapling system with the jaws in an open configuration.

With reference to FIG. 1, an embodiment of surgical stapling system is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. A staple reload 50 can be positioned in the jaw assembly. While the illustrated surgical stapling system is illustrated with a powered handle, it is contemplated that the elongate shaft 20 and jaw assembly 30 can be interchangeably used in a stapling system including a mechanical stapler handle. For example, it is contemplated that the various embodiments of elongate shaft assembly 20 and jaw assembly 20 described herein can be used interchangeably with either the powered handle assemblies described in U.S. patent application Ser. No. 15/486,008, entitled "SURGICAL STAPLER HAVING A POWERED HANDLE," filed Apr. 12, 2017, currently pending, and the mechanical manually actuated handle assemblies described in U.S. patent application Ser. No. 15/485,620, entitled "SURGICAL STAPLER HAVING ARTICULATION MECHANISM," filed Apr. 12, 2017, currently pending. These applications are incorporated by reference herein in their entireties.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end to a distal end. The elongate shaft 20 defines a central longitudinal axis, L, of the surgical stapler 10 extending between the proximal end and the distal end.

Figure 2A:
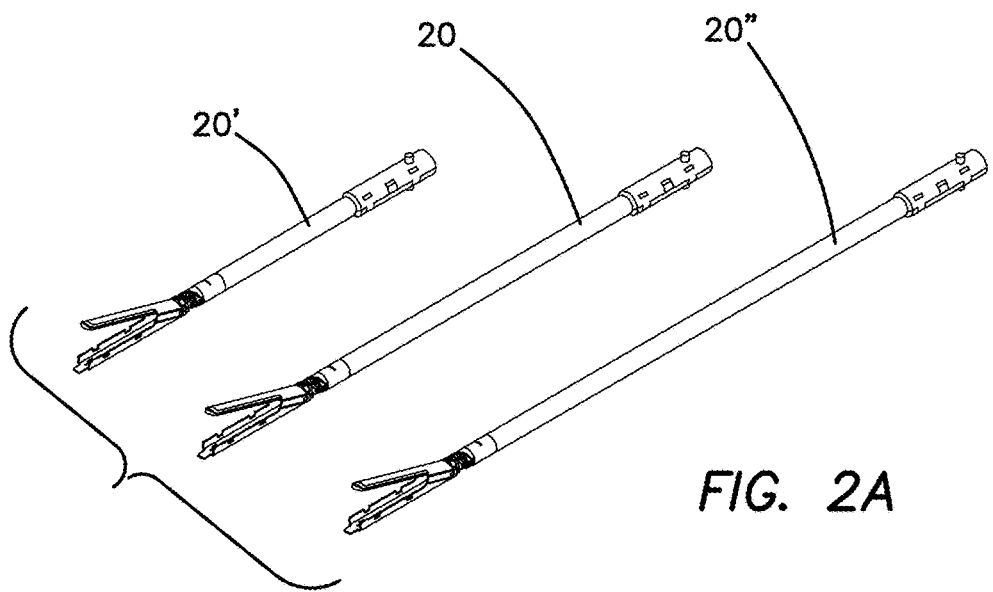
FIG. 2a is a perspective view of several embodiments of shaft assembly for the surgical stapling system of FIG. 1.

With reference to FIG. 2a, it is contemplated that the stapling system can include an elongate shaft having a desired length. While the features of the jaw assembly and handle coupling described herein can be substantially similar for each of these shaft assemblies, the shaft bodies can be scalable. For example, a stapling system can include a relatively short elongate shaft 20', a mid-length elongate shaft 20, or a relatively long elongate shaft 20". Each of these shaft lengths can have particular applicability for a subset of patients or procedures. For example, the short elongate shaft 20' can be useful in pediatric procedures, and the long elongate shaft 20" can be useful in bariatric procedures.

Figure 2B:
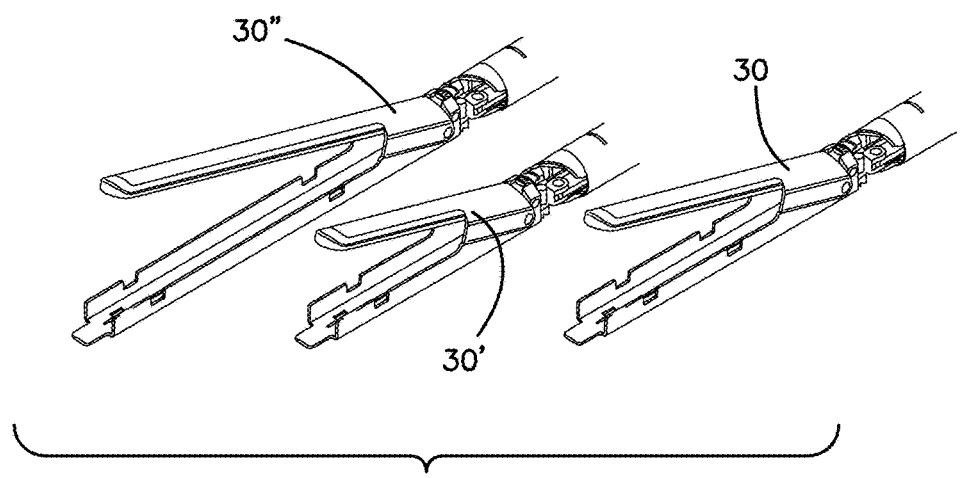
FIG. 2b is a perspective view of several embodiments of jaw assembly for the surgical stapling system of FIG. 1.

With reference to FIG. 2b, it is contemplated that the stapling system can include a jaw assembly having a desired length. While the features of the jaw assembly and articulation joint described herein can be substantially similar for each of these shaft assemblies, the jaw assemblies bodies can be scalable. For example, a stapling system can include a relatively short jaw assembly 30', a mid-length jaw assembly 30, or a relatively long jaw assembly 30". Each of these jaw assemblies can have particular applicability for a subset of patients or procedures. In certain embodiments, it is contemplated that the jaw assembly have a length of approximately 45 mm. In other embodiments, it is contemplated that the jaw assembly have a length of approximately 60 mm.

With continued reference to FIG. 1, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the jaw assembly 30 is articulable with respect to the elongate shaft 20.

With continued reference to FIG. 1, in the illustrated embodiment, the jaw assembly 30 can be actuated from an open configuration (FIG. 1) to a closed configuration to a stapling configuration by an actuation member or beam that is longitudinally slidable within the elongate shaft. In an initial position, the beam can be positioned at the distal end of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples from the reload positioned in the first jaw 32.

With continued reference to FIG. 1, in the illustrated embodiment, the handle assembly is coupled to the elongate shaft 20 at the proximal end of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configuration such as, for example, scissors-grip configurations, or in-line configurations. As further described in greater detail below, the handle assembly 40 houses an actuation mechanism configured to selectively advance an actuation shaft responsive to movement of the movable handle 44.

Figure 3:
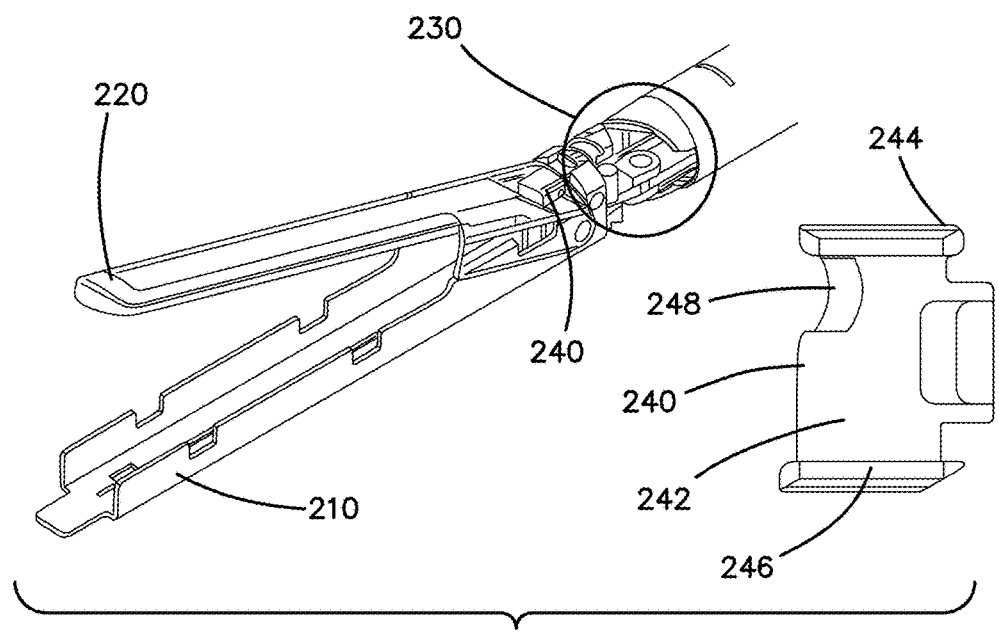
FIG. 3 is a perspective view of a jaw assembly at the distal end of the shaft assembly for the surgical stapling system of FIG. 1.

With reference to FIG. 3, an embodiment of jaw assembly at the distal end of the shaft assembly 20 is illustrated. In the illustrated embodiment, the jaw assembly comprises a reload support 210 articulably coupled to the distal end of the shaft assembly 20 at an articulation joint 230. An anvil 220 is pivotably coupled to the reload support 210 and defines a top jaw of the jaw assembly 30. A firing member 240 can slide within the jaw assembly to initially close the anvil 220 relative to the reload support 210, then fire staples from a reload. In some embodiments, the firing member 240 has an I-beam configuration with a vertical beam 242 spanning between two horizontally-protruding flanges 244, 246. Advantageously, with an I-beam configuration, one horizontal flange 244 can engage a channel in the anvil 220 and the other flange 246 can engage a channel in the reload or reload support to close the jaw assembly then maintain a desired closed spacing of the jaw assembly when the firing member is advanced distally. In some embodiments, the firing member 240 can comprise a cutting blade 248 formed on or mounted to the vertical beam in an I-beam configuration. This cutting blade can separate tissue as staples are fired to form staple lines on both sides of the separated tissue.

Figure 4:
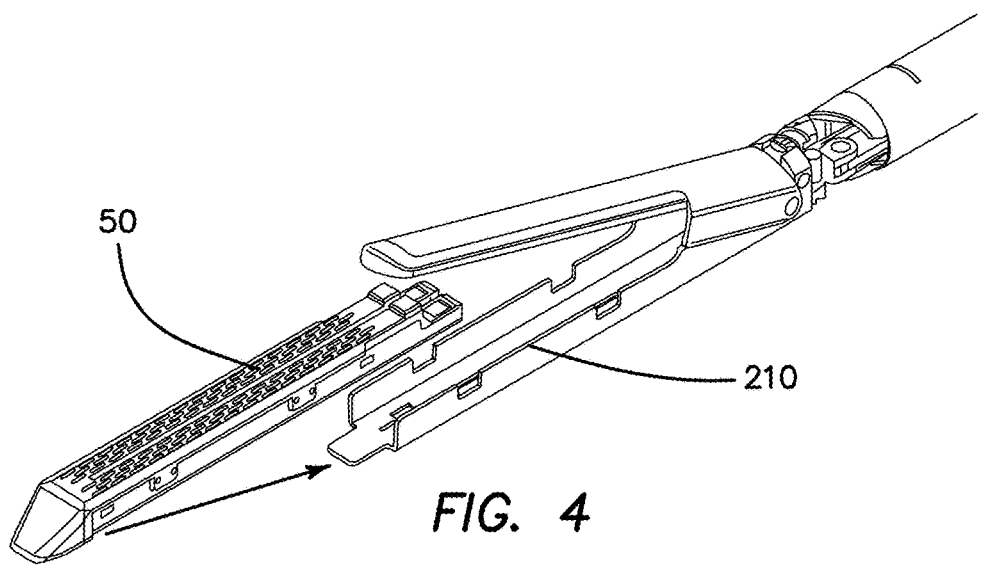
FIG. 4 is a perspective view of the jaw assembly of FIG. 3 with a staple reload.
Figure 5:
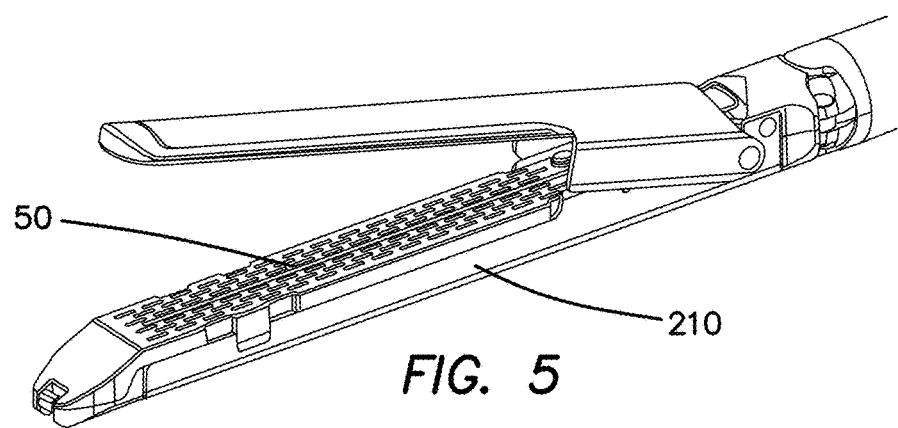
FIG. 5 is a perspective view of the jaw assembly of FIG. 3 with a staple reload inserted.
Figure 6A:
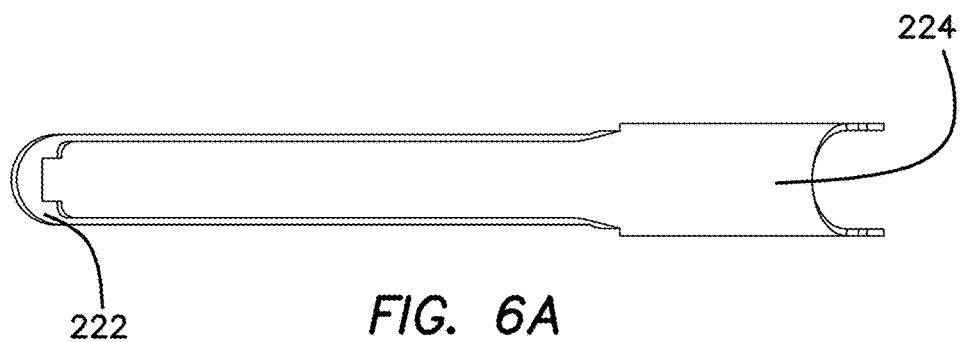
FIG. 6A is a top view of an anvil for the jaw assembly of FIG. 3.
Figure 6B:
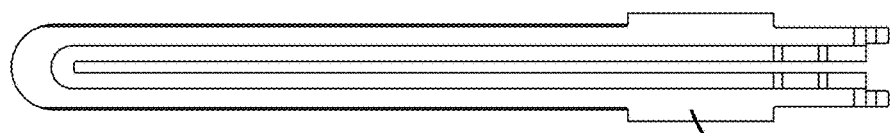
FIG. 6B is a top view of an anvil plate for the jaw assembly of FIG. 3.
Figure 7:
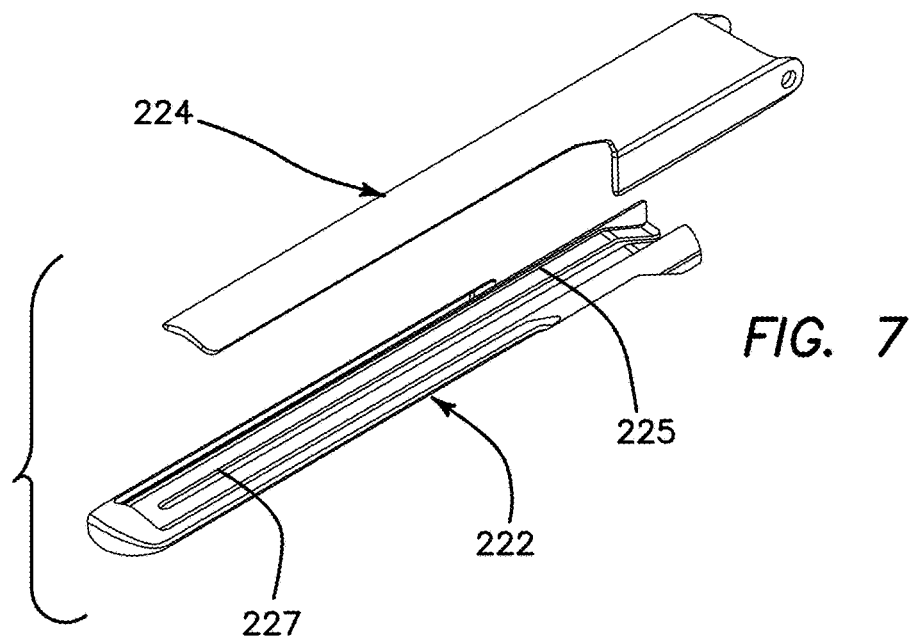
FIG. 7 is an exploded perspective view of the anvil of the jaw assembly of FIG. 3.

With reference to FIGS. 4 and 5, the reload support 210 can be sized to receive and retain a disposable reload 50. The reload 50 can be lowered and moved proximally into the reload support 210 until mating features on the reload engage corresponding features on the reload support 210.

Figure 8:
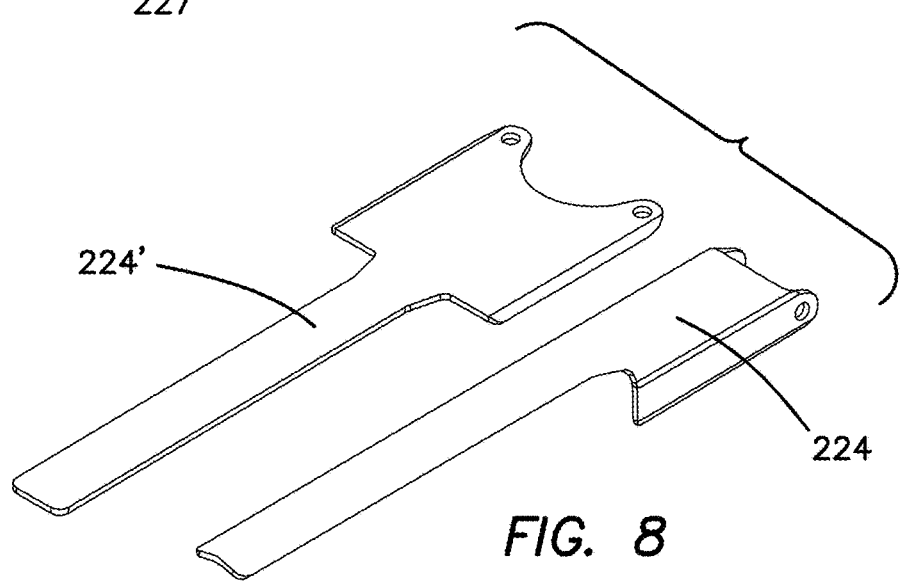
FIG. 8 is a perspective view of the top jaw of the jaw assembly of FIG. 3 in an initial state and a formed state.

With reference to FIGS. 6A, 6B, 7, and 8, various aspects of the anvil 220 of the jaw assembly 30 are illustrated. In certain embodiments, the anvil 220 comprises an anvil plate 222 coupled to a top surface 224. The anvil plate can comprise a longitudinal channel 225 formed therein in which a horizontal flange of the firing member rides and a longitudinal slot 227 formed through the longitudinal channel 225 in which the vertical beam of the firing member rides. The top surface 224 can be formed of a sheet of material that is subsequently formed to overly the anvil plate. (FIG. 8 illustrates the flat sheet 224' and shaped top surface 224). Advantageously, the addition of the top surface 224 to the anvil plate 222 enhances the strength of the anvil of the jaw assembly.

Figure 9:
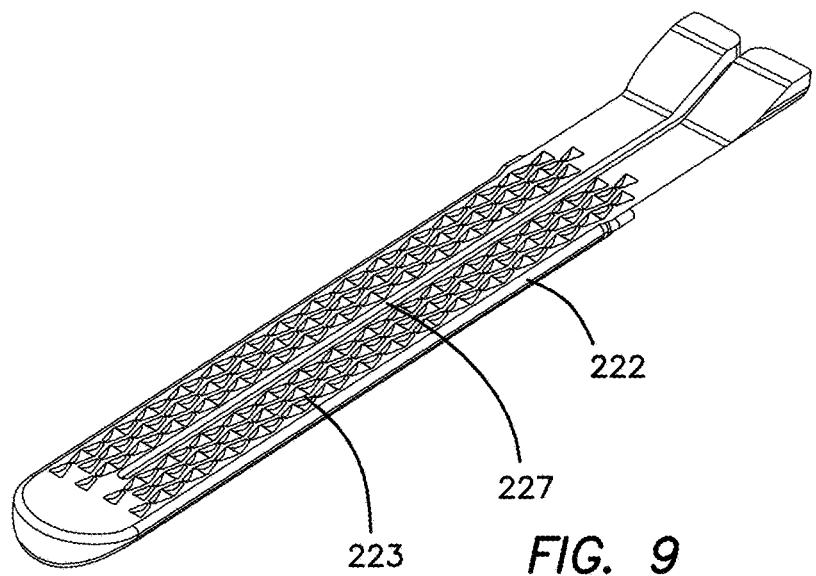
FIG. 9 is a perspective view of the anvil surface of the jaw assembly of FIG. 3.
Figure 10:
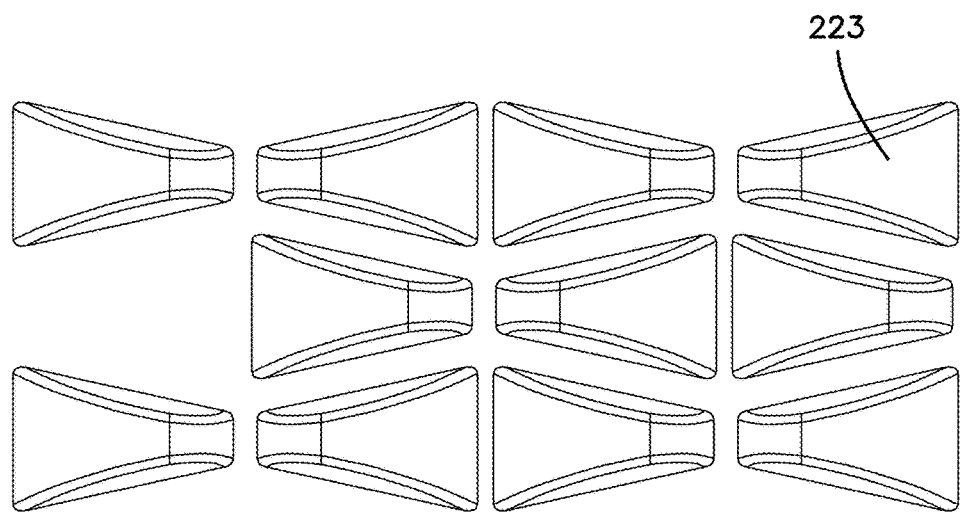
FIG. 10 schematic diagram of staple recesses in the anvil surface of FIG. 9.

With reference to FIGS. 9 and 10, various aspects of the anvil plate 222 of the jaw assembly 30 are illustrated. The anvil plate comprises a plurality of staple forming pockets 223 thereon. In the illustrated embodiment, the staple forming pockets 223 are positioned in two arrays of three rows with the arrays positioned on either side of the slot for the firing member. Thus, the stapler can form two sets of three linear rows of staples with the sets separated by divided tissue. In other embodiments, it is contemplated that the anvil can include staple forming pockets configured to form other numbers and configurations of staples. The staple forming pockets have a tapered configuration with a relatively large staple entry side narrowing to a relatively small staple formation side. Advantageously, this tapered configuration can guide staples to complete formation and reduce the incidence of poorly formed staples. Adjacent rows of staples can be longitudinally offset from one another such that the relatively wide entry sides of all of the rows are offset from one another to reduce the overall width of the sets of staple rows.

Figure 11A:
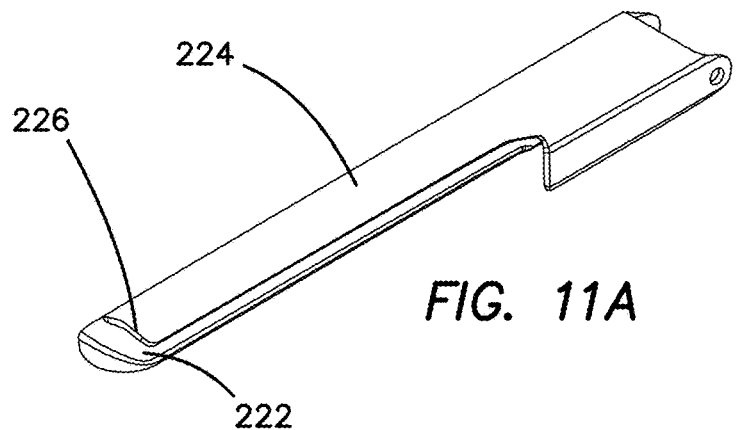
FIG. 11A is a perspective view of the anvil of the jaw assembly of FIG. 3.
Figure 11B:
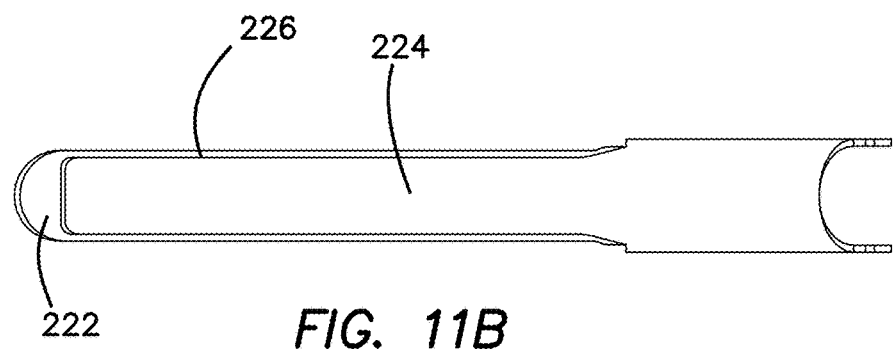
FIG. 11B is a top view of the anvil of the jaw assembly of FIG. 3.

With reference to FIGS. 11a and 11b, in certain embodiments of anvil 220, the top surface 224 can be coupled to the anvil plate 222 by a welding operation along a weld line 226. Advantageously, this closed anvil formed by the welding operation covers the channel for the firing member.

Figure 12:
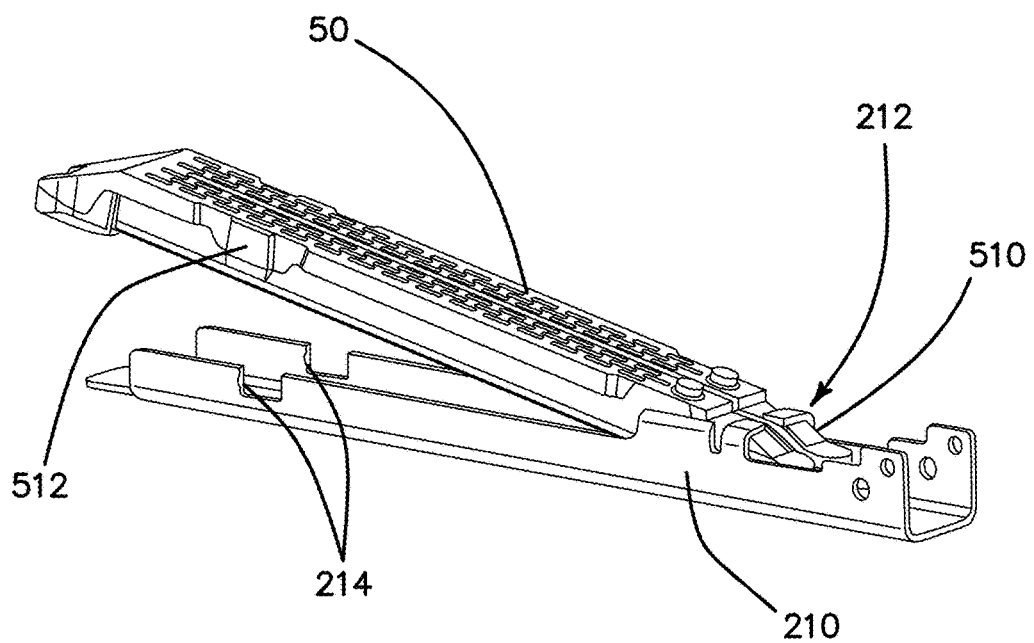
FIG. 12 is a perspective view of the reload support of the jaw assembly of FIG. 3 with a reload partially inserted.
Figure 13:
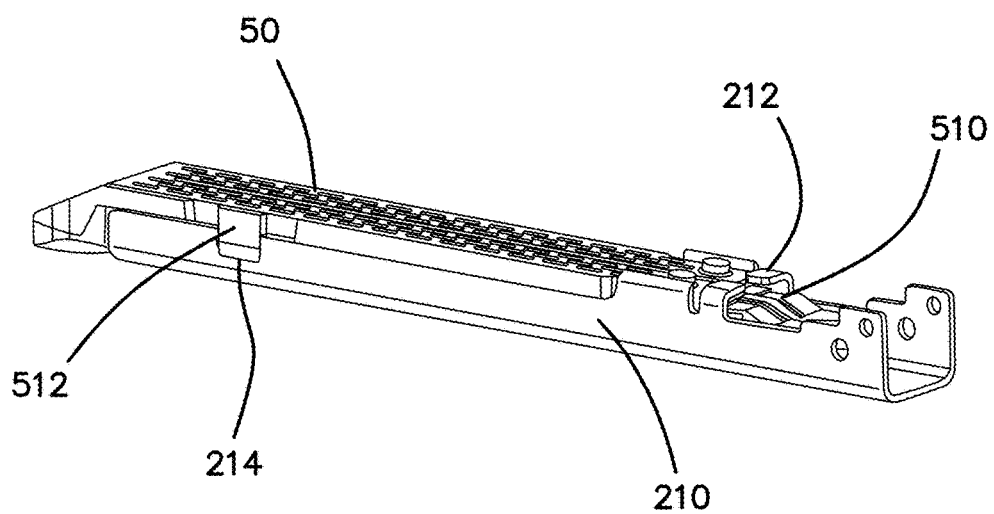
FIG. 13 is a perspective view of the reload support of the jaw assembly of FIG. 3 with a reload inserted.
Figure 16:
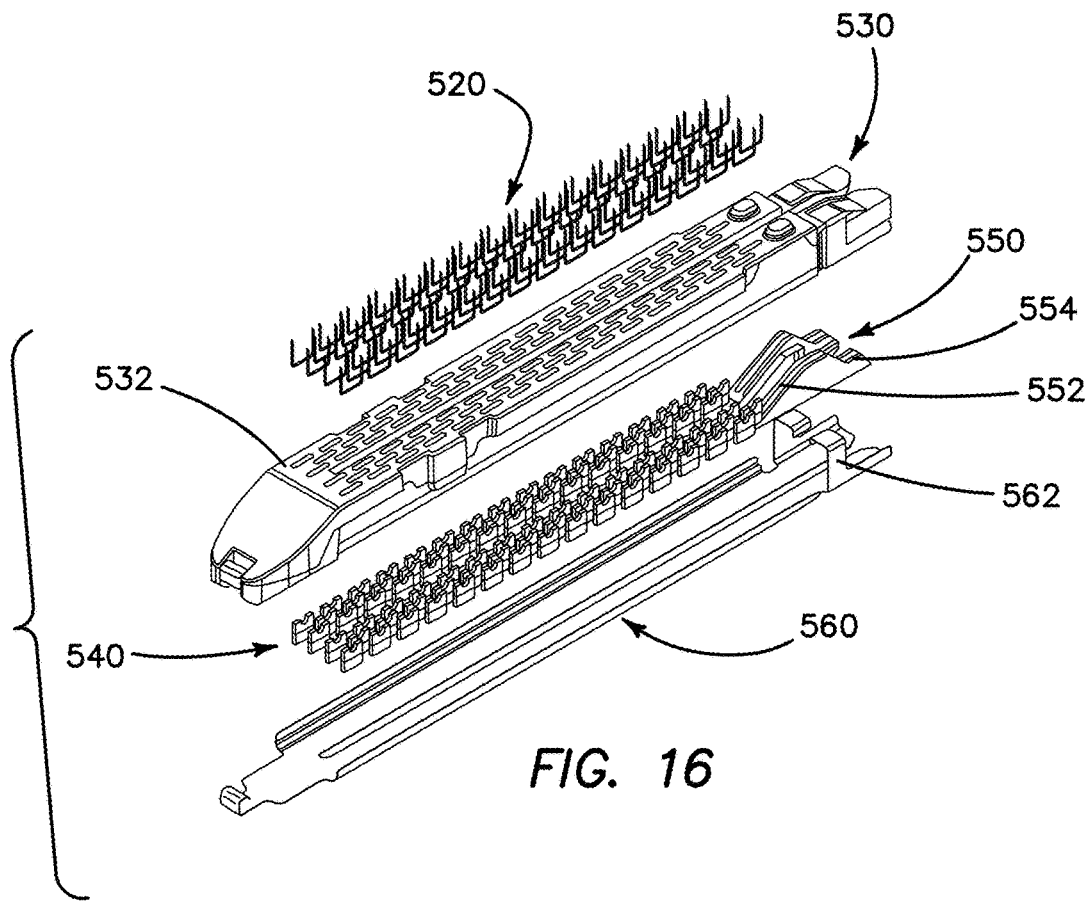
FIG. 16 is an exploded perspective view of a reload for use in the staple system of FIG. 1.
Figure 17:
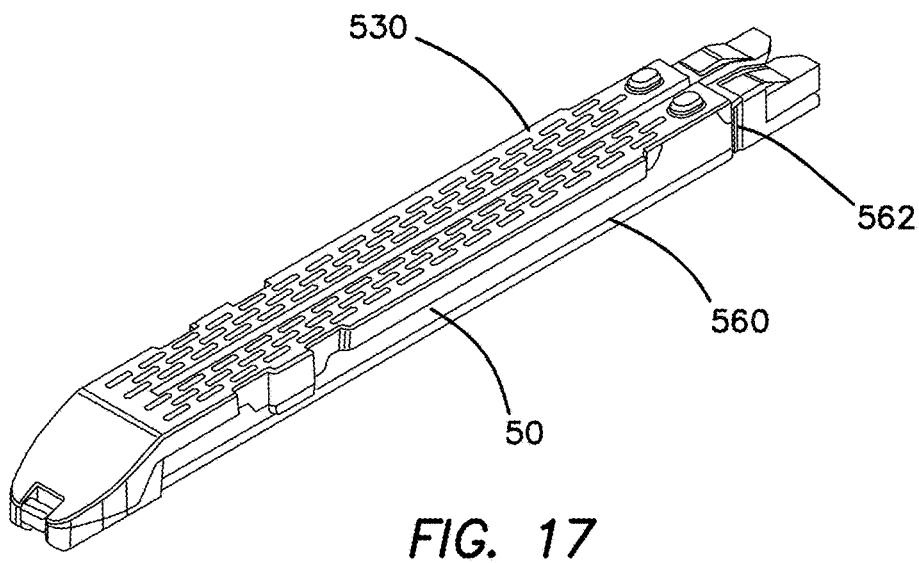
FIG. 17 is an upper perspective view of the reload for use in the staple system of FIG. 1.
Figure 18:
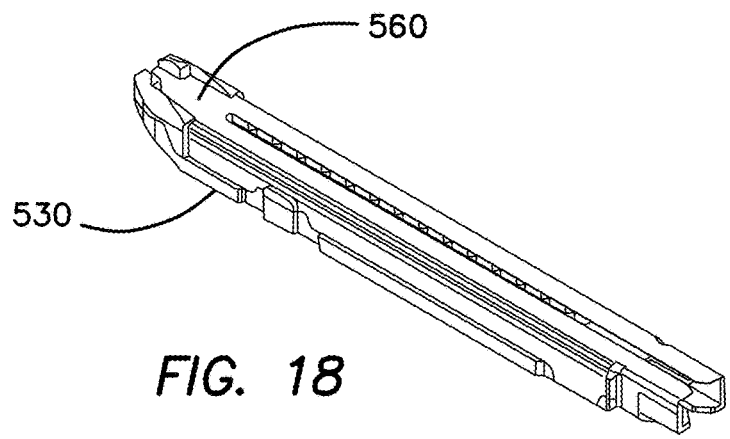
FIG. 18 is a lower perspective view of the reload for use in the staple system of FIG. 1.
Figure 19:
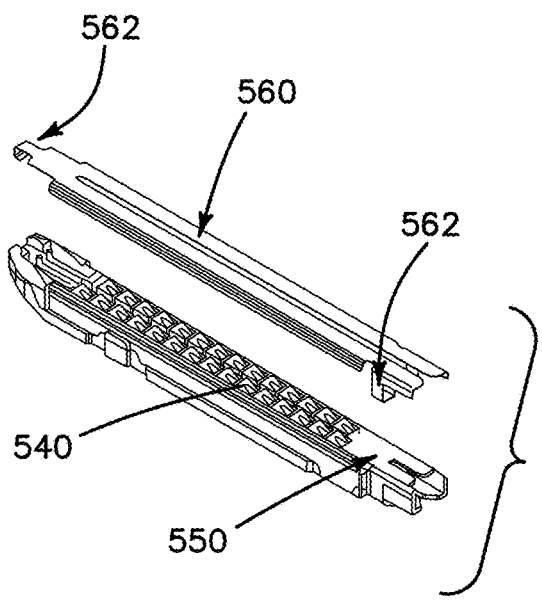
FIG. 19 is an exploded lower perspective view of the reload for use in the staple system of FIG. 1.

With reference to FIGS. 12 and 13, insertion of a reload 50 in the reload support 210 is illustrated. The reload support can comprise proximal jaw tabs 212 that protrude radially inwardly from side walls of the reload support 210 adjacent the proximal end thereof. The reload can comprise a relatively short, tapered proximal deck 510 sized to be positioned under and retained by the proximal jaw tabs. Moreover, the reload 50 can include retention tabs 512 protruding laterally outwardly adjacent a distal end thereof. The reload support 210 can comprise a corresponding pair of retention recesses 214 sized and configured to receive the retention tabs when the reload is positioned in the reload support.

Figure 14:
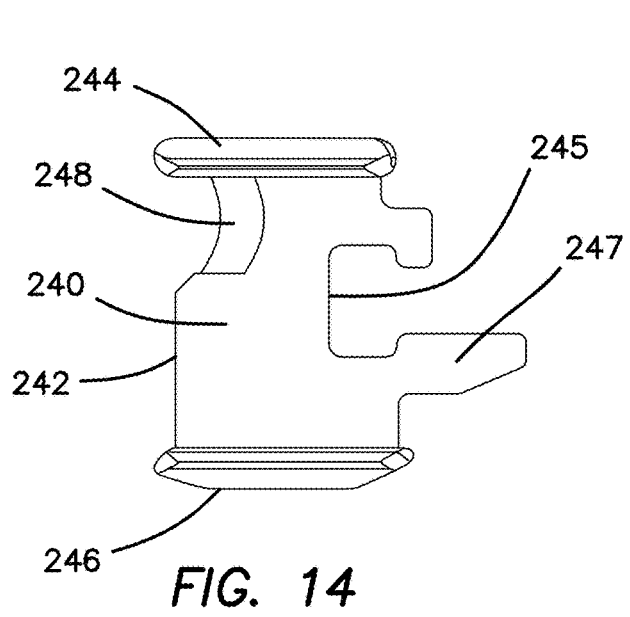
FIG. 14 is a side view of a closure beam of the jaw assembly of FIG. 3.
Figure 15:
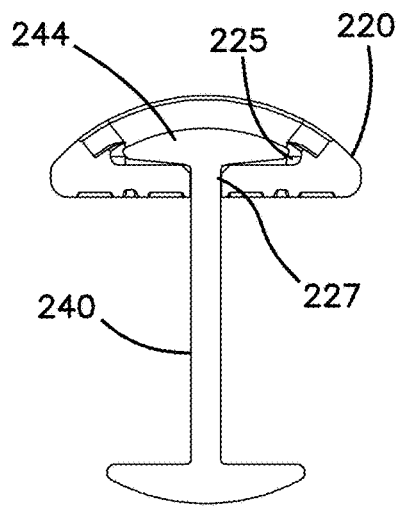
FIG. 15 is a partial cut-away front view of the closure beam of FIG. 14 with a flange thereof positioned in a channel in the anvil of the jaw assembly of FIG. 3.

With reference to FIGS. 14 and 15, an embodiment of firing member 240 having an I-beam configuration is illustrated. In the illustrated embodiment, The firing member comprises a vertical beam 242 having a cutting blade formed therein at a leading edge. The cutting blade comprises a curved cutting blade 248. A trailing edge of the firing member 240 comprises a drive member interface 245 such as a cutout or protrusion to allow the firing member to be securely coupled with the drive member extending through the elongate shaft. The trailing edge of the firing member 240 can further comprise a lockout interface 247, such as a proximally extending 'tail' that can position a reload lockout in an unlocked configuration when the firing member is in a proximal position. The firing member further comprises an upper horizontal flange 244 configured to ride in the channel 225 of the anvil and a lower horizontal flange 246 configured to engage the reload or reload support. As illustrated in FIG. 15, although the firing member has a general I-beam configuration, in some embodiments the horizontal flanges are curved or tapered such to conform with a shape of the channel 225 in the anvil. In some embodiments, the firing member 240 can further be configured to reduce friction during a firing sequence such as by surface finishing operations, addition of a film lubricant, or deposition of a low-friction surface on the firing member, channel, or both.

With reference to FIGS. 16-19, an embodiment of reload 50 for use in the stapling system is illustrated. The reload 50 comprises a plurality of staples 520 positioned in a corresponding plurality of staple pockets 532 formed in a cartridge 530. The staple pockets 532 are arranged in two sets of three rows each with each set separated by a slot formed through the cartridge 530. The staples 520 rest in a plurality of staple pushers 540 underlying the staple pockets 532. A slider 550 having a ramp 552 corresponding to each row of staple pusher 540 and a lockout tail 554 is positioned at the proximal end of the reload. The slider 550 is longitudinally slidable within the reload responsive to movement of the firing member. A jacket 560 underlies the cartridge and maintains the staples and staple pushers in the staple pockets. The jacket can have protruding hooks 562 to engage the cartridge.

Figure 20:
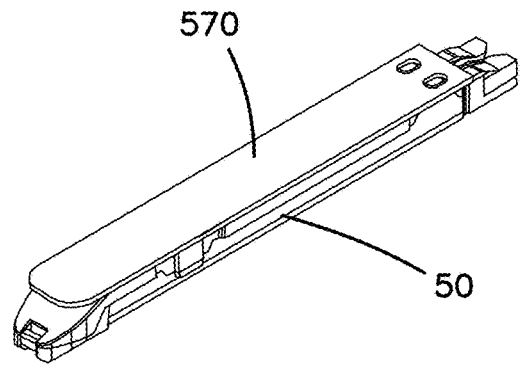
FIG. 20 is a perspective view of the reload for use in the staple system of FIG. 1.

With reference to FIG. 20, in some embodiments, the reload 50 can include a shipping cover 570 covering an upper surface of the cartridge. Advantageously, the shipping cover 570 can prevent one or more of the staples from becoming dislodged from or misaligned within the staple pockets before the reload is used. The shipping cover 570 is removed before the reload 50 is positioned in the reload support.

Figure 21:
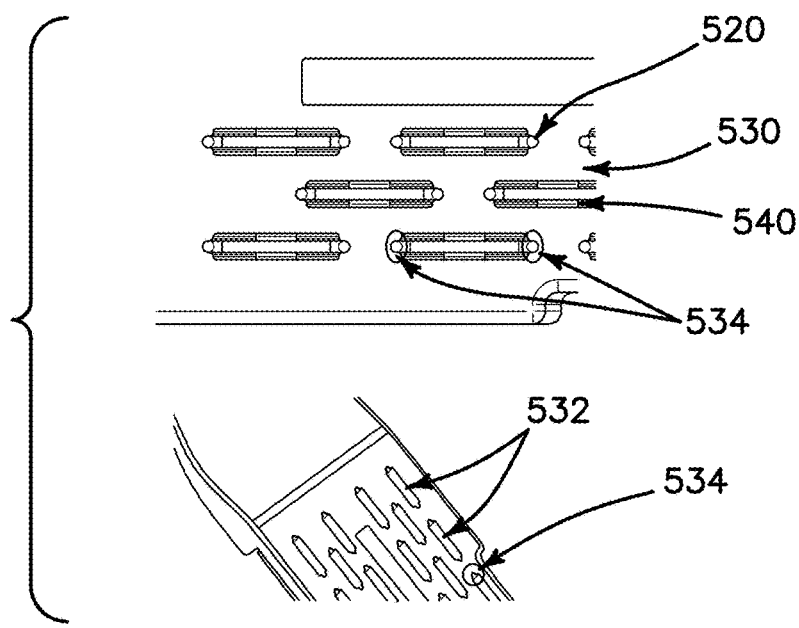
FIG. 21 is a top detail view of the reload for use in the staple system of FIG. 1.
Figure 22:
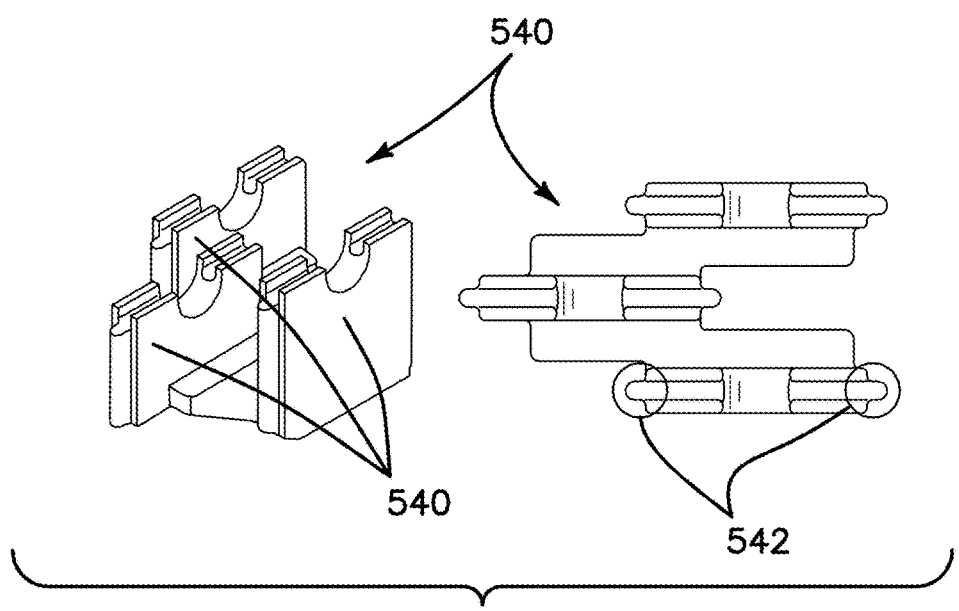
FIG. 22 is a perspective view of a staple pusher for the reload of FIG. 16.
Figure 23:
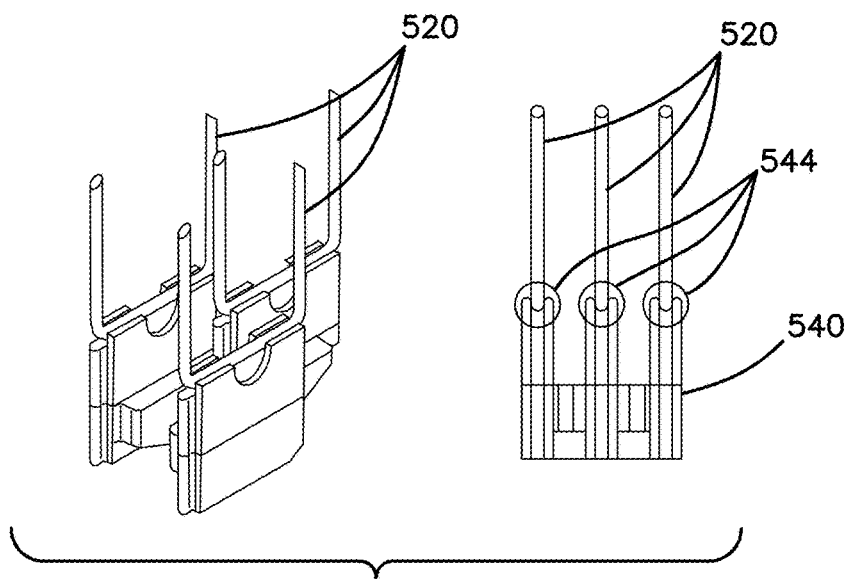
FIG. 23 is a perspective view of a staple pusher of the reload of FIG. 16.
Figure 24:
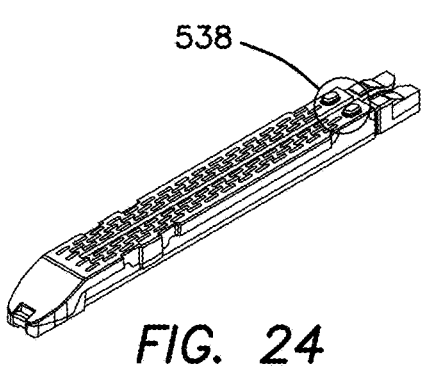
FIG. 24 is a perspective view of the reload for use in the staple system of FIG. 1.

With reference to FIGS. 21-23, in some embodiments, the reload 50 can include certain staple alignment and retention features. For example the staple pockets 532 formed in the cartridge 530 can include staple guides 534 at ends thereof to receive legs of the staples 520 positioned therein. The staple pushers 540 can additionally include nubs 542 sized and configured to ride in the staple guides 534. As illustrated, in certain embodiments, the staple pushers 540 can be formed in groups of three such that one staple pusher 540 can push a single staple in each of three adjacent rows of staples. Moreover, an upper surface 544 of each of the staple pushers 540 can include a staple saddle configuration to relatively securely receive a staple. Secure positioning of the staples 520 in the staple pushers 540 and engagement of the staple legs and nubs 542 of the staple pushers with the staple guides can advantageously reduce the incidence of misaligned or malformed staples.

Figure 25:
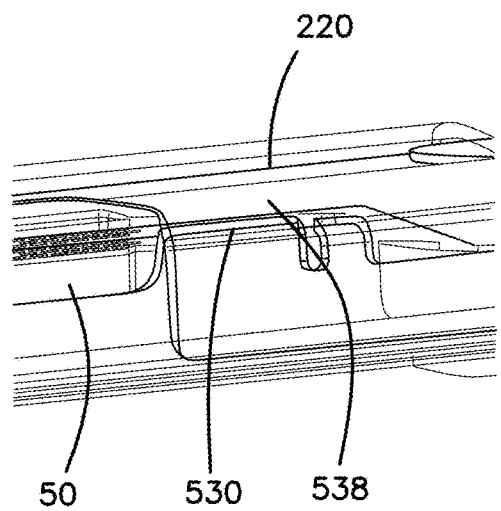
FIG. 25 is a partial cut-away view of the jaw assembly of FIG. 3 in a closed configuration.
Figure 26:
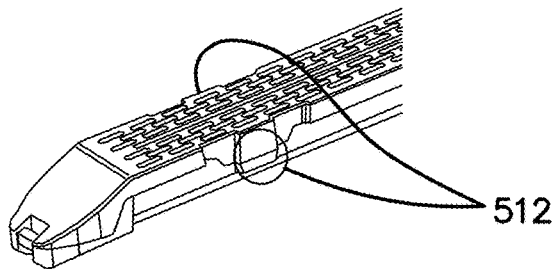
FIG. 26 is a perspective view of the reload of FIG. 16.
Figure 27:
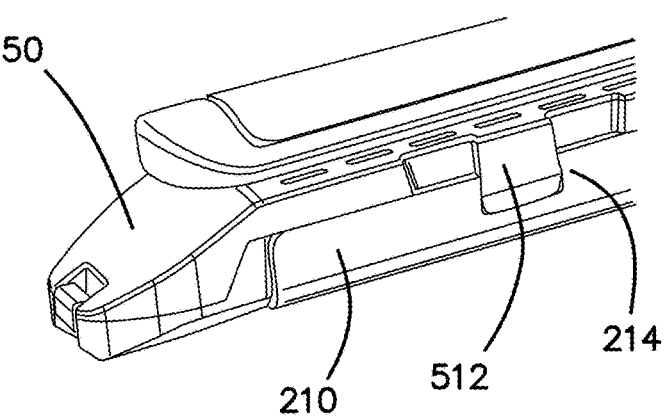
FIG. 27 is a perspective view of the jaw assembly of FIG. 3 in a closed configuration with a reload inserted.
Figure 28:
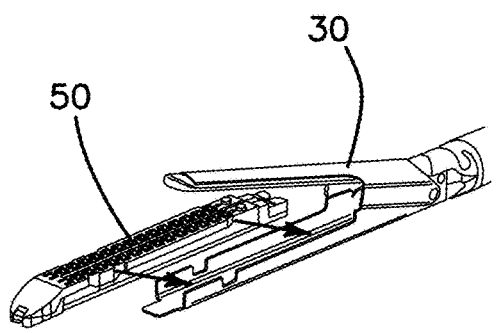
FIG. 28 is a perspective view of the jaw assembly of FIG. 3 with a reload positioned for insertion.
Figure 29:
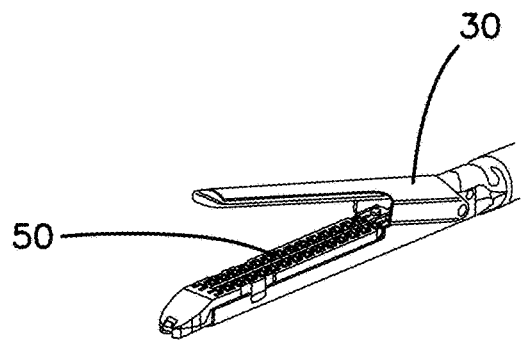
FIG. 29 is a perspective view of the jaw assembly of FIG. 3 with a reload inserted.
Figure 30:
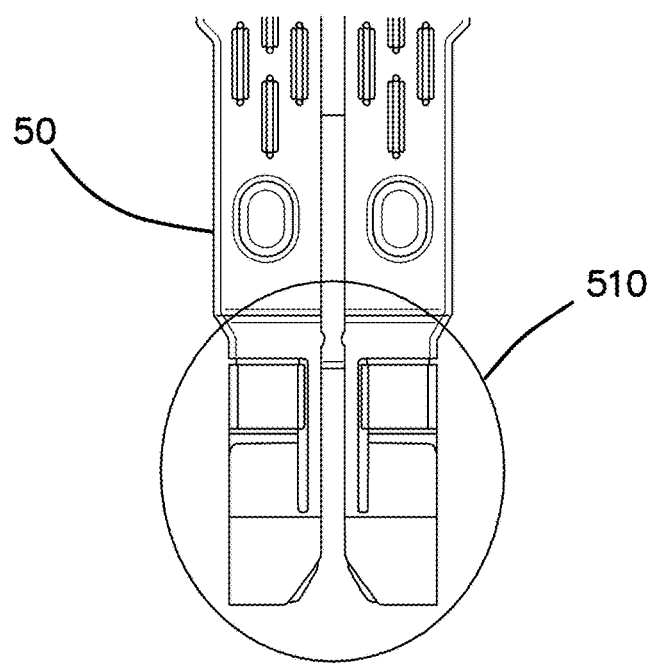
FIG. 30 is a top view of the reload of FIG. 16.
Figure 31:
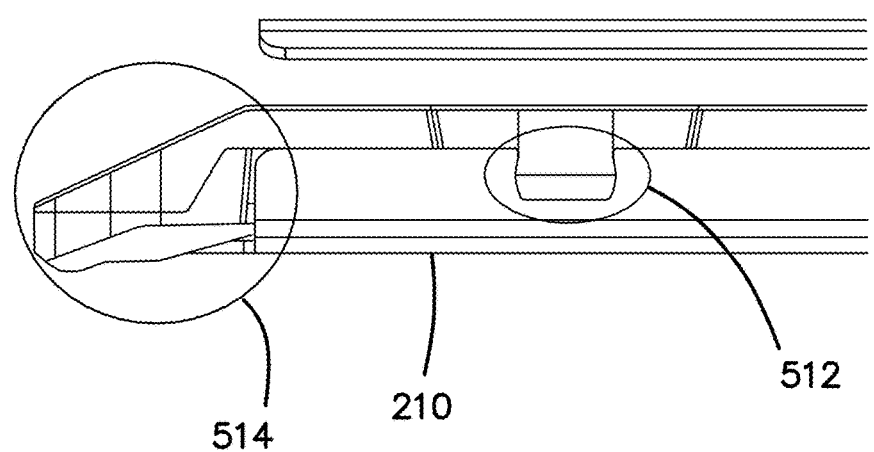
FIG. 31 is a side view of the jaw assembly of FIG. 3 with a reload inserted.
Figure 32A:
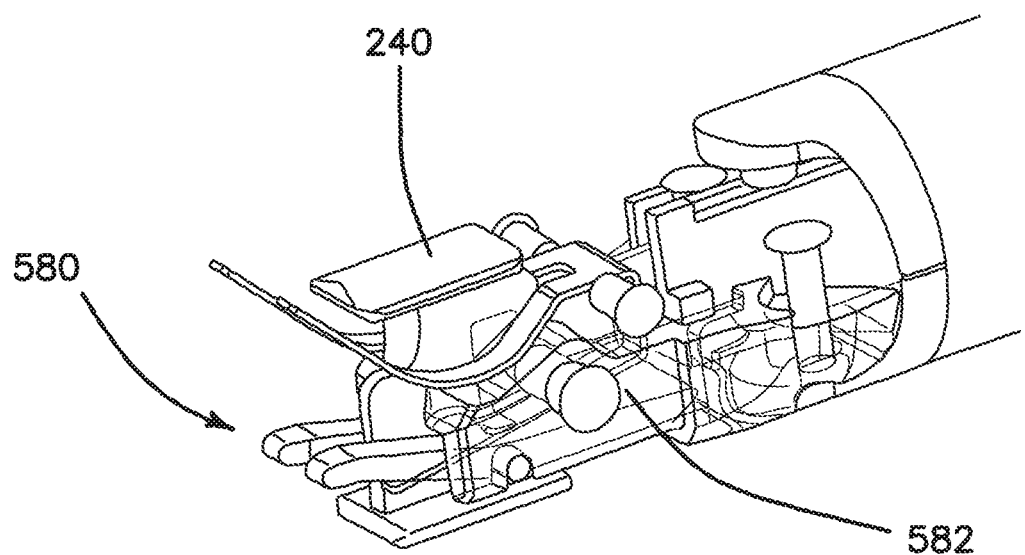
FIG. 32A is a perspective view of a reload lockout mechanism of the shaft assembly.
Figure 32B:
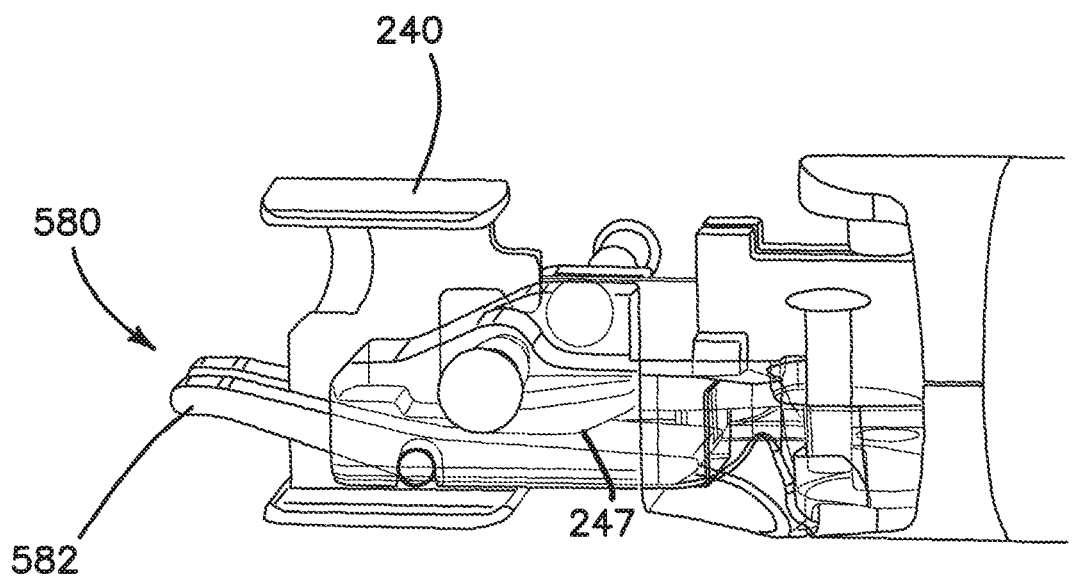
FIG. 32B is a side view of the reload lockout mechanism of the shaft assembly.

With reference to FIGS. 24-31, in various embodiments, the reload 50 and jaw assembly can be configured to be securely coupled to one another to align the staple pockets on the reload 50 with the staple forming pockets on the anvil and maintain the position of the reload 50 in the jaw assembly during staple firing. The reload 50 can include upwardly protruding bosses 538 at a proximal end thereof (FIG. 24) that define a tissue gap between the anvil 220 and an upper surface of the cartridge 530 of the reload 50 with the jaw assembly in a closed configuration (FIG. 25). Moreover, the retention tabs 512 formed adjacent the distal end of the reload (FIG. 26) are positioned within recesses 214 of the reload support 210 and prevent the reload from shifting distally during a firing operation. Thus, the reload 50 can be rapidly and securely coupled to the reload support 210 (FIGS. 28-29). Additionally, a proximal end of the cartridge 530 can taper to a reduced height to further facilitate placement on the reload support (FIG. 30). Furthermore, the cartridge can be configured with a lowered distal end 514 having a profile protruding below the reload support (FIG. 31). This lowered profile ensures secure engagement of the reload with the reload support.

Figure 33:
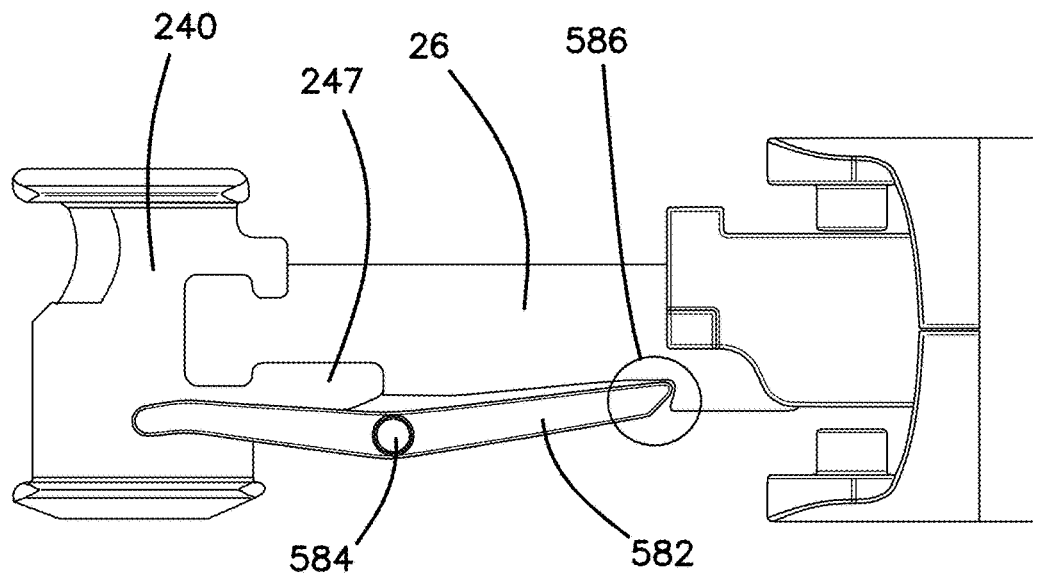
FIG. 33 is a side view of the reload lockout mechanism of the shaft assembly in a locked configuration.
Figure 34:
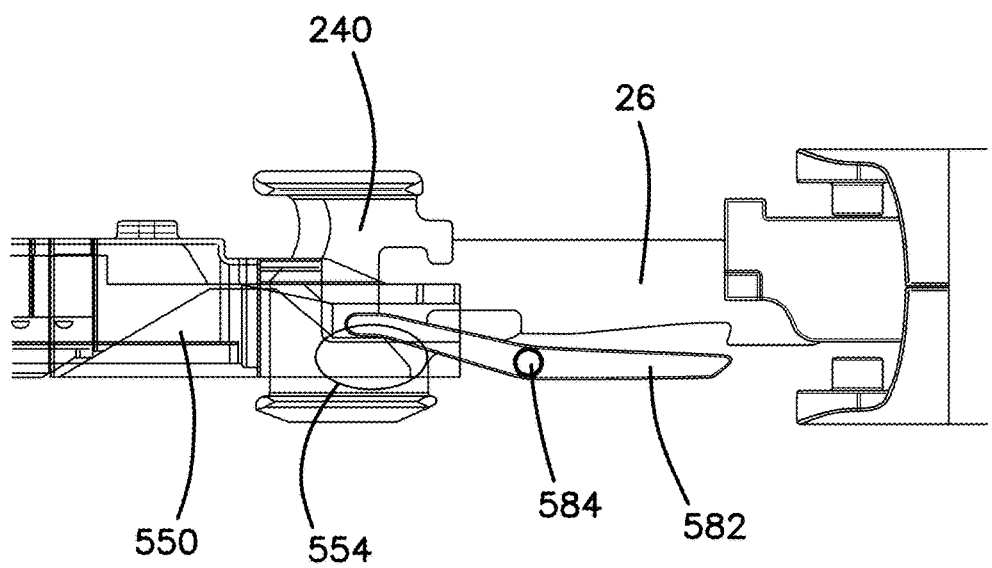
FIG. 34 is a side view of the reload lockout mechanism of the shaft assembly in an unlocked configuration.

With reference to FIGS. 32A, 32B, and 33-34, in certain embodiments, the jaw assembly can comprise a reload lockout mechanism 580. The reload lockout mechanism 580 can prevent advancement of the firing member if no reload is positioned within the jaw assembly or if an empty reload is positioned within the jaw assembly. The reload lockout mechanism 580 includes a lockout lever 582 pivotally coupled to the reload support. An axis defined by the pivot extends generally transverse to the longitudinal axis of the elongate shaft. With the firing member 240 fully retracted such that the jaw assembly is in an open configuration, a tail 247 extending proximally from the firing member 240 maintains the lockout lever 582 pivoted to the unlocked position. In the illustrated embodiment, a proximal portion of the lockout lever 582 proximal the pivot is forked or bifurcated to receive the firing member 240 therein such that the tail 247 can act on a surface of the lockout lever 582 distal the pivot. If no reload is inserted, an attempt to advance the firing member 240 will allow the lockout lever to pivot about a pivot point 584 from the unlocked position to the locked position as the tail 247 of the firing member is advanced distally along the lockout lever. (FIG. 33). With the lockout lever 582 in the locked position, a proximal, locking end 586 of the lockout lever interferes with a lock recess on the drive member 26, preventing further distal movement of the drive member.

With continued reference to FIGS. 32A, 32B, and 33-34, if an unfired reload is inserted into the reload support (FIG. 34), a tail 554 extending proximally from the slider 550 engages a distal end of the lockout lever 582. As illustrated, the tail 554 acts on a lower surface of a distal portion of the lockout lever 582 distal the pivot point. This engagement of the slider tail 554 with the distal end of the lockout lever 582 pivots the proximal end of the lookout lever 582 away from the drive member 26 even once the tail 247 of the firing member 240 is no longer acting on the proximal portion of the lockout lever. Accordingly, the drive member 26 and firing member 240 can be distally advanced to fire the staples from the reload. Upon completion of a firing stroke, the slider 550 remains at a distal end of the reload. Thus if the jaw assembly is returned to the open configuration, withdrawing the firing member, the fired reload should be removed and a new unfired reload should be inserted to unlock the reload lockout.

Figure 35:
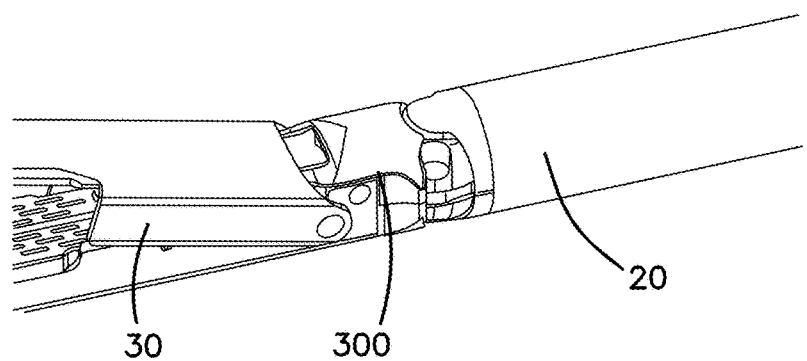
FIG. 35 is a perspective view of the distal end of the elongate shaft at an articulation joint connection with the jaw assembly of FIG. 3.
Figure 36:
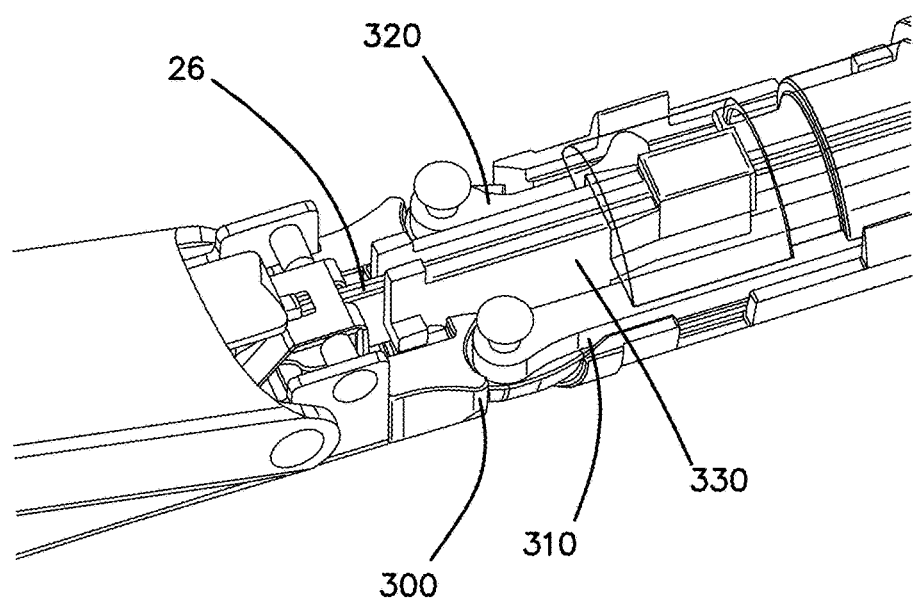
FIG. 36 is a partial cut-away perspective view of one embodiment of articulation joint at the distal end of the elongate shaft.
Figure 37:
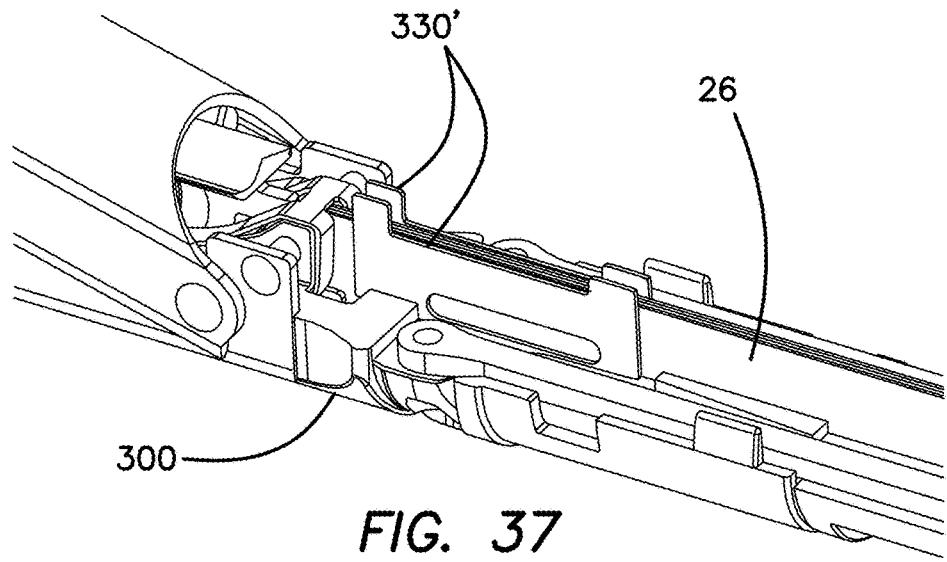
FIG. 37 is a partial cut-away perspective view of one embodiment of articulation joint at the distal end of the elongate shaft.

With reference to FIGS. 35-37, an embodiment of articulation joint 300 to couple the jaw assembly 30 to the distal end of the elongate shaft 20 is illustrated. In the illustrated embodiment, the articulation joint 300 comprises an articulation rod 310 pivotably coupled to the jaw assembly laterally offset from a central longitudinal axis of the shaft assembly. A pivot joint is positioned along the central longitudinal axis. The articulation joint 300 further comprises a support link 320 pivotably coupled to the jaw assembly laterally offset from the central longitudinal axis of the shaft and opposite the articulation rod. The drive beam 26 extends longitudinally along the central longitudinal axis between the articulation rod 310 and the support link 320. At least a segment of the drive beam 26 extending through the articulation joint 300 is flexible. In some embodiments, the drive beam 26 can be coupled to a flexible segment comprising a stack of shim material, which is flexible while maintaining desired force transmission capabilities for a staple firing operation. The articulation joint can further comprise one or more drive member bearings 330 positioned laterally outwardly of the drive beam 26. In some embodiments, the drive bearings 330 can comprise a flexible plastic material (FIG. 36). In other embodiments, the drive bearings 330' can be comprised of a metal shim material (FIG. 37). Advantageously, the metal shim drive bearing 330' can be keyed into the shaft to provide support to the flexible segment of the drive member. Moreover, the metal shim bearings can have a relatively low profile configuration. The metal shim bearings can include a low friction coating such as a TEFLON coating to reduce friction during a firing.

Figure 38A:
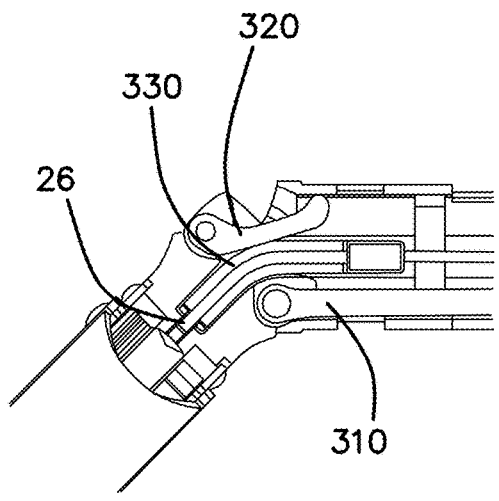
FIG. 38A is a partial cut-away top view of the articulation joint of FIG. 36 in an articulated position.
Figure 38B:
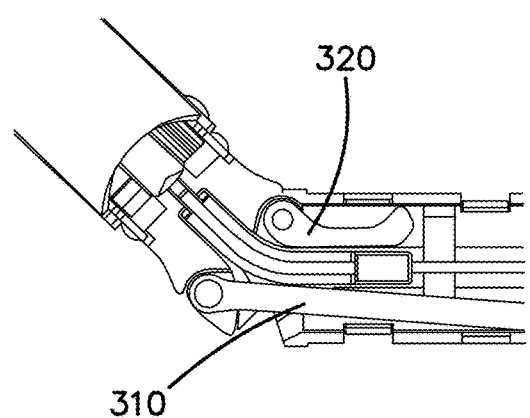
FIG. 38B is a partial cut-away top view of the articulation joint of FIG. 36 in another articulated position.

With reference to FIGS. 38A-38B, articulation of the articulation joint to position the jaw assembly in a first articulation position and a second articulation position are illustrated. The articulation rod 310 can be translated proximally (FIG. 38A) or distally (FIG. 38B) relative to the shaft. The lateral offset positioning of the articulation rod 310 articulates the jaw assembly relative to the shaft responsive to translation of the articulation rod. The support link 320 opposite the articulation rod 310 is passive, but can guide articulation motion of the jaw assembly and can advantageously assist in maintaining the flexible portion of the drive beam 26 towards the center of the shaft at the articulation joint, preventing the flexible portion of the drive beam 26 from buckling at the articulated bend at the articulation joint. In other embodiments, the articulation joint can include two articulation rods instead of an articulation rod and support link. In embodiments with two articulation rods, an articulation latch mechanism can be positioned in the shaft to prevent undesired articulation once a staple firing operation has commenced. For example, a latch or brake mechanism can retain the articulation rods from further movement once the drive beam 26 is translated distally.

Figure 39:
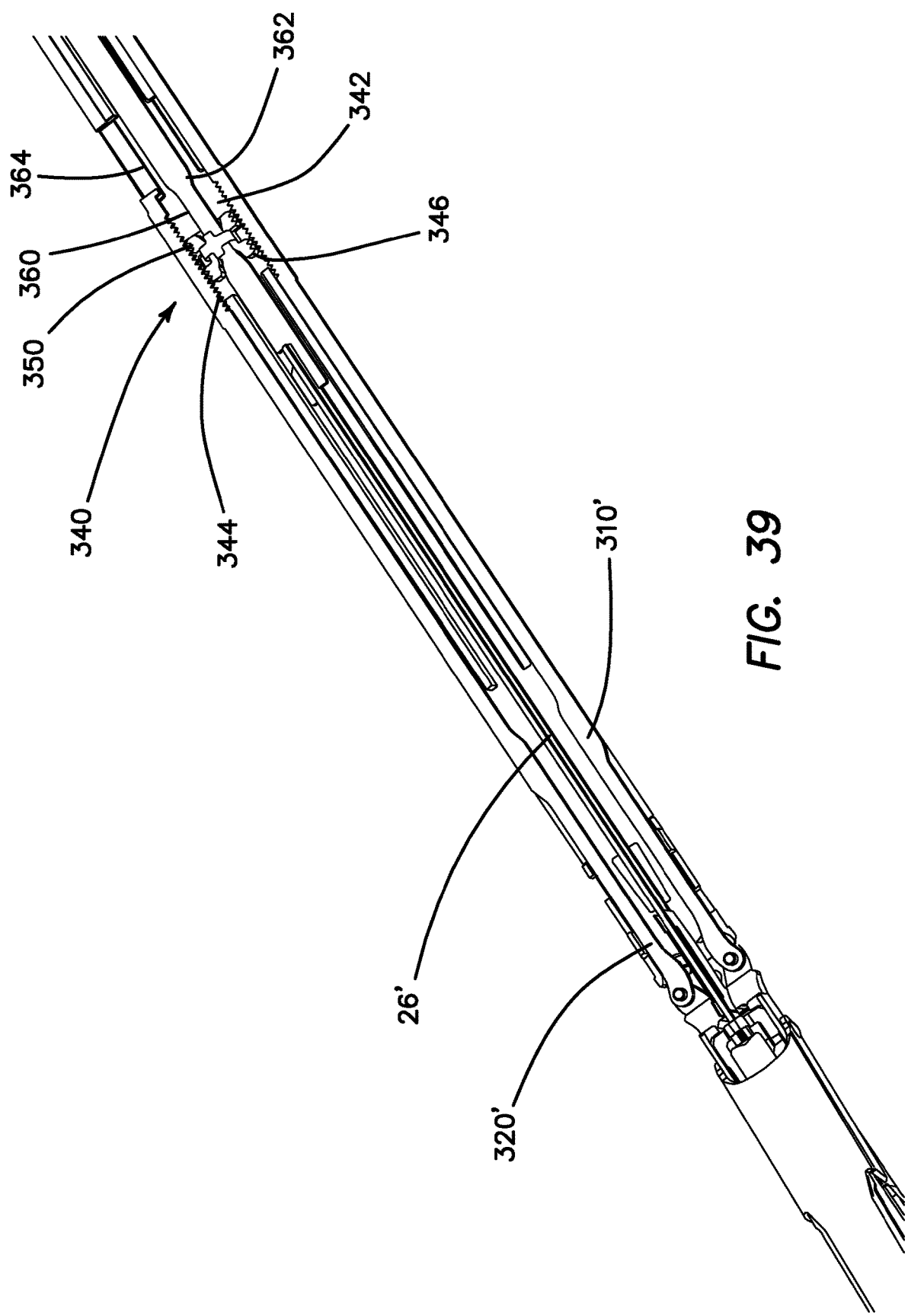
FIG. 39 is a partial cut-away perspective view of another embodiment of articulation joint at the distal end of the elongate shaft.
Figure 40:
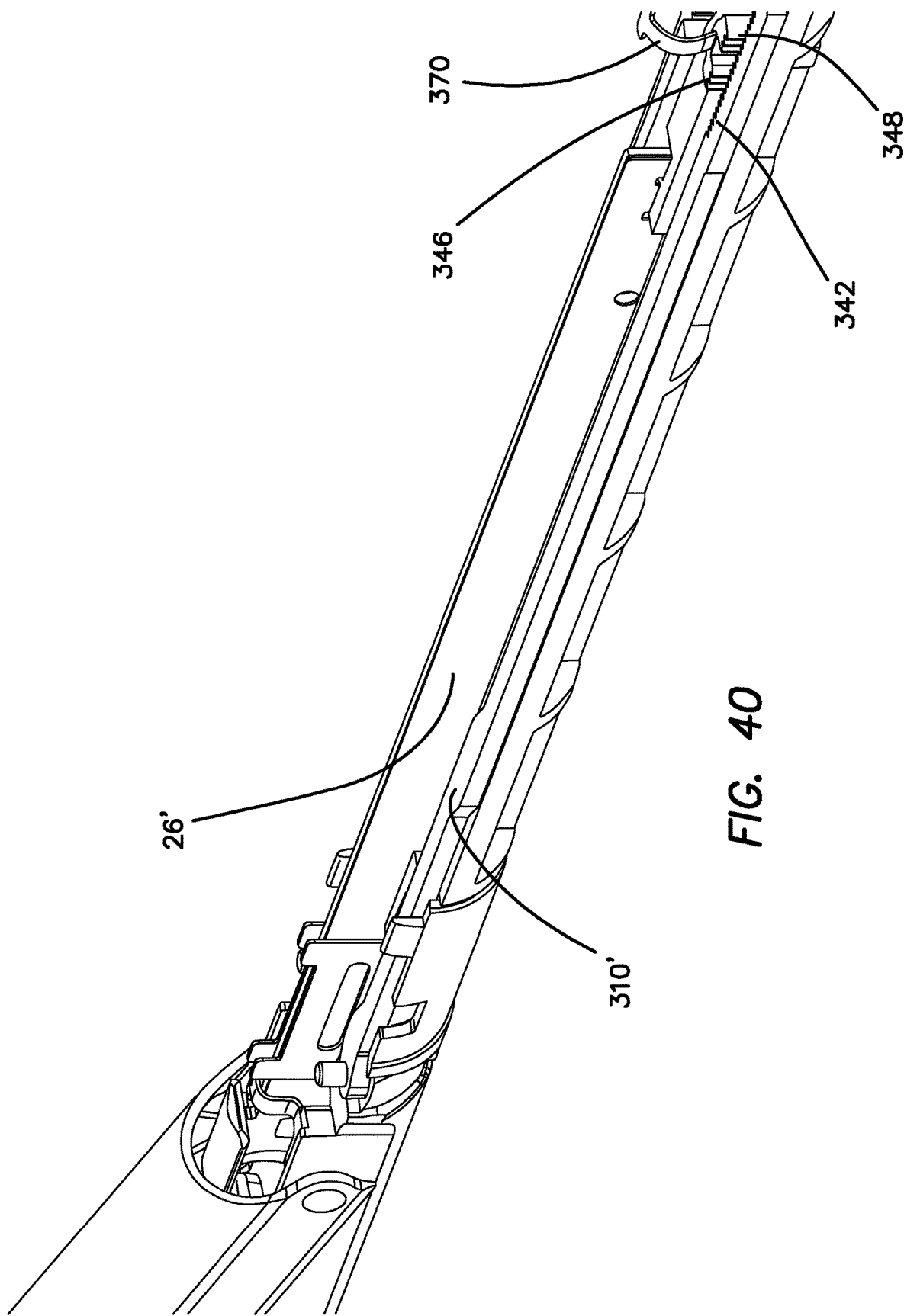
FIG. 40 is a partial cut-away perspective view of the embodiment of articulation joint of FIG. 39 at the distal end of the elongate shaft.

With reference to FIGS. 39-40, another embodiment of articulation joint 300' to couple the jaw assembly 30 to the distal end of the elongate shaft 20 is illustrated. The articulation joint 300' comprises an articulation latch mechanism 340 positioned in the elongate shaft. In the illustrated embodiment, the articulation joint 300' comprises an articulation rod 310' pivotably coupled to the jaw assembly laterally offset from a central longitudinal axis of the shaft assembly. A pivot joint is positioned along the central longitudinal axis. The articulation joint 300' further comprises a support link 320' pivotably coupled to the jaw assembly laterally offset from the central longitudinal axis of the shaft and opposite the articulation rod. The drive beam 26' extends longitudinally along the central longitudinal axis between the articulation rod 310' and the support link 320'. At least a segment of the drive beam 26' extending through the articulation joint 300' is flexible. In some embodiments, the drive beam 26' can be coupled to a flexible segment comprising a stack of shim material, which is flexible while maintaining desired force transmission capabilities for a staple firing operation. The articulation joint can further comprise one or more drive member bearings 330 positioned laterally outwardly of the drive beam 26'. In some embodiments, the drive bearings 330 can comprise a flexible plastic material (FIG. 36). In other embodiments, the drive bearings 330' can be comprised of a metal shim material (FIG. 37). Advantageously, the metal shim drive bearing 330' can be keyed into the shaft to provide support to the flexible segment of the drive member. Moreover, the metal shim bearings can have a relatively low profile configuration. The metal shim bearings can include a low friction coating such as a TEFLON coating to reduce friction during a firing.

Figure 41:
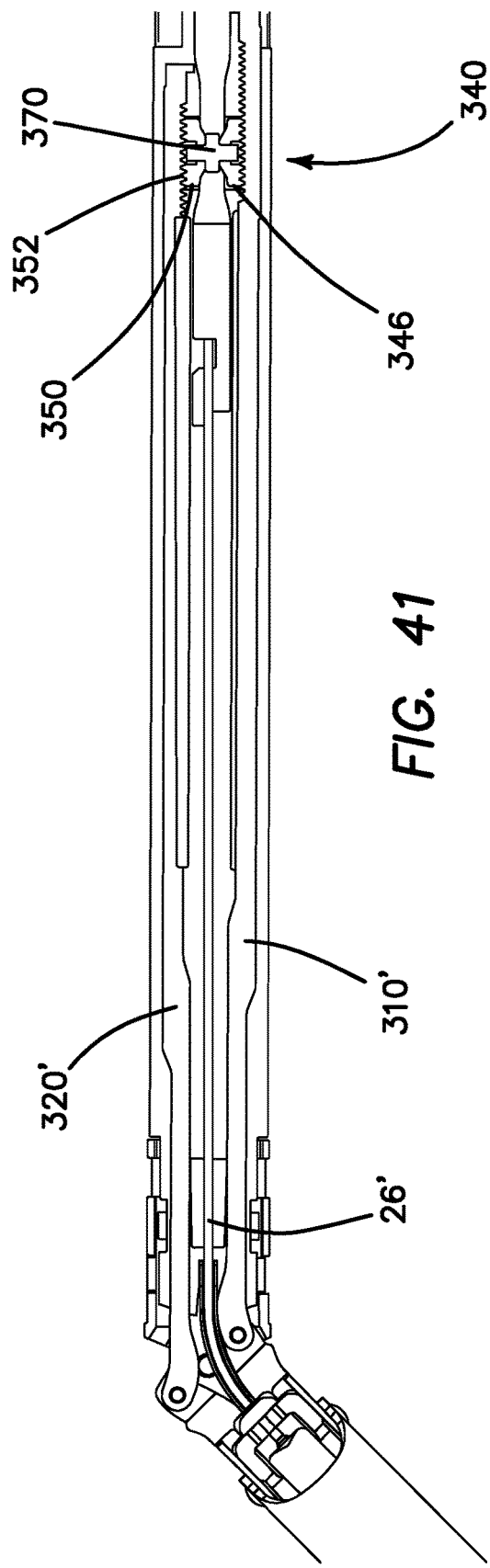
FIG. 41 is a partial cut-away top view of the articulation joint of FIG. 39 in an articulated position.
Figure 42:
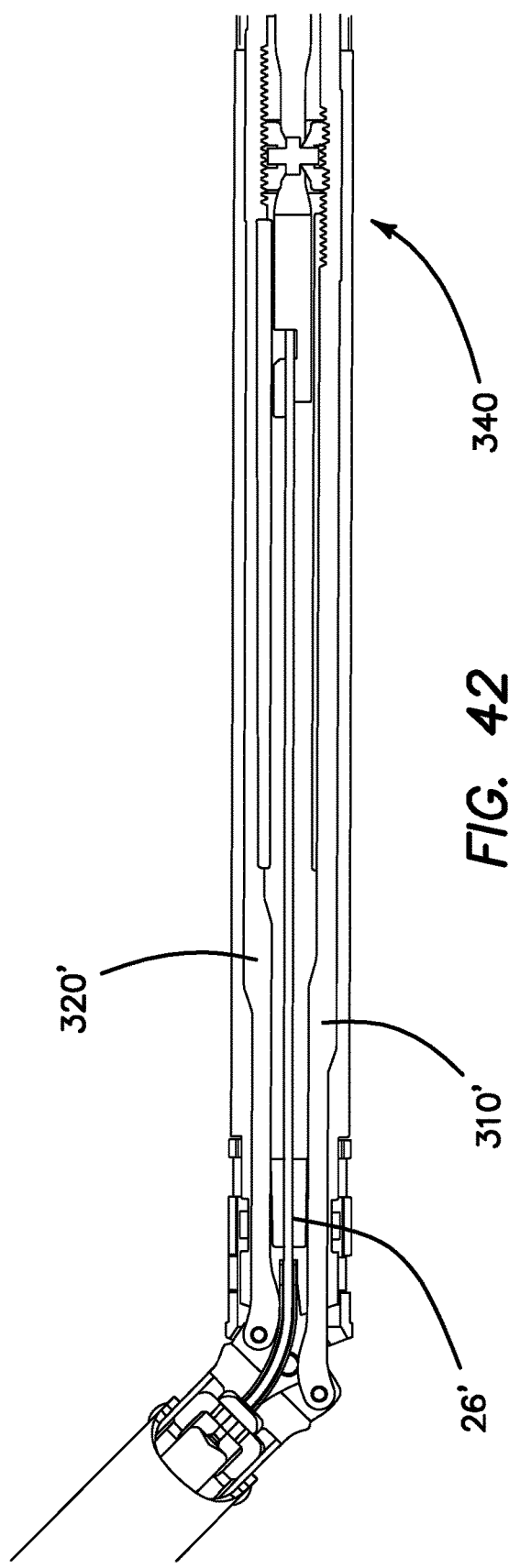
FIG. 42 is a partial cut-away top view of the articulation joint of FIG. 39 in another articulated position.

With reference to FIGS. 41-42, articulation of the articulation joint to position the jaw assembly in a first articulation position and a second articulation position are illustrated. The articulation rod 310' can be translated proximally (FIG. 41) or distally (FIG. 42) relative to the shaft. The lateral offset positioning of the articulation rod 310' articulates the jaw assembly relative to the shaft responsive to translation of the articulation rod. The support link 320' opposite the articulation rod 310' is passive, but can guide articulation motion of the jaw assembly and can advantageously assist in maintaining the flexible portion of the drive beam 26' towards the center of the shaft at the articulation joint, preventing the flexible portion of the drive beam 26' from buckling at the articulated bend at the articulation joint. In other embodiments, the articulation joint can include two articulation rods instead of an articulation rod and support link.

With reference to FIGS. 39-43, the articulation latch mechanism 340 or brake mechanism of the articulation joint 300' can retain the articulation rod and support link from further movement once the drive beam 26' is translated distally. In the illustrated embodiment, the latch mechanism 340 is positioned within the elongate shaft between the proximal end and the distal end thereof. The articulation latching mechanism 340 has an unlatched configuration in which the articulation rod and the support link are slidable within the elongate shaft. Thus, with the articulation latching mechanism in the unlatched configuration, a user can articulate the jaw assembly relative to the elongate shaft by operation of an articulation control on the handle assembly. The articulation latching mechanism 340 further comprises a latched configuration (FIG. 43), wherein the articulation latching mechanism engages the articulation rod and the support link to prevent longitudinal sliding of the articulation link and the support link relative to the elongate shaft. Thus, in the latched configuration, the jaw assembly is retained in an articulated position and the user is prevented from articulating the jaw assembly relative to the elongate shaft.

With continued reference to FIGS. 39-43, in the illustrated embodiment, the articulation latching mechanism 340 comprises a first latch surface, such as a first plurality of teeth 342 formed on the articulation rod 310'. As illustrated, the first plurality of teeth 342 is positioned within the elongate shaft between the proximal end and the distal end of the articulation rod 310'. The articulation latching mechanism 340 can further comprise a second latch surface, such as a second plurality of teeth 344 formed on the support link 320'. As illustrated, in the embodiment of elongate shaft assembly having a latching articulation mechanism, the support link 320' can extend proximally within the shaft through the articulation latching mechanism 340. In the illustrated embodiment, the second plurality of teeth 344 is positioned between the proximal end of the support link and the distal end of the support link adjacent the proximal end of the support link 320'.

In the illustrated embodiment, the articulation latching mechanism 340 further comprises a first shoe 346 having a mating surface such as a first pawl surface 348 formed thereon. The first pawl surface 348 is sized and configured to be engageable with the first plurality of teeth 342. The first shoe 346 can have a deployment surface opposite the mating surface, the deployment surface is in sliding engagement with the drive beam 26'. The articulation mechanism 340 can further comprise a second shoe 350 having a mating surface such as a second pawl surface 352 formed thereon. The second pawl surface 352 is sized and configured to be engageable with the second plurality of teeth 344. The second shoe 350 can have a deployment surface opposite the mating surface, the deployment surface in sliding engagement with the drive beam 26'. The articulation latching mechanism 340 can further comprise a latching profile formed on the drive beam 26' between the proximal end and the distal end thereof and positioned within the elongate shaft. In the illustrated embodiment, the drive beam 26' comprises a recess segment 360 formed therein, a tapered or ramped segment 362 proximal the recess segment, and a latching segment 364 proximal the ramped segment. The recess segment 360 has a first width in a direction generally perpendicular to the longitudinal axis of the elongate shaft, and the latching segment 364 has a second width greater than the first width. The articulation latching mechanism can further comprise a biasing member such as a spring clip 370 coupled to the first and second shoes and biasing the shoes 346, 350 out of engagement with the first and second pluralities of teeth 342, 344. The spring clip can also maintain engagement of the deployment surfaces of the shoes 346, 350 with the latching profile of the drive beam 26'.

Figure 43:
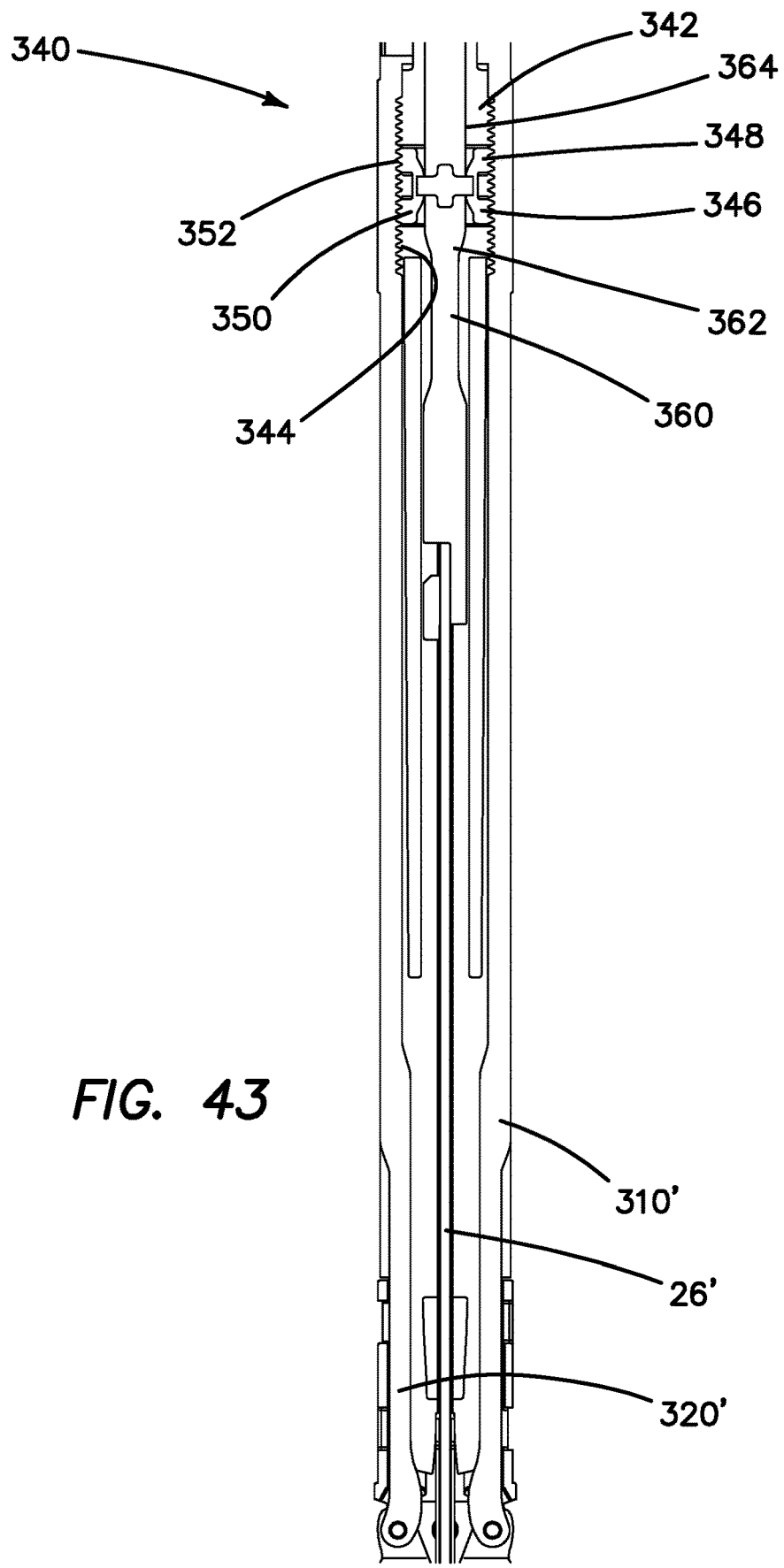
FIG. 43 is a partial cut-away top view of the articulation joint of FIG. 39 in a latched position.
Figure 44:
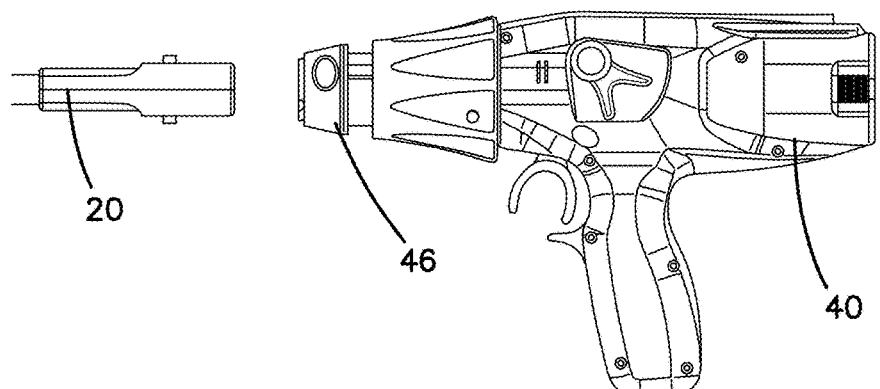
FIG. 44 is a side view of the proximal end of the shaft assembly positioned adjacent a handle assembly for the stapler system of FIG. 1.

With continued reference to FIGS. 39-43, in operation, the articulation latching mechanism 340 can initially be positioned in the unlatched configuration (FIGS. 39-42) such that the jaw assembly can be articulated to a desired orientation relative to the elongate shaft. In this initial positioning, the drive beam 26' is in a proximal position relative to the elongate shaft, corresponding to an open or partially closed configuration of the jaw assembly. In the unlatched configuration, the first and second shoes 346, 350 are positioned adjacent the recess segment 360 of the drive beam 26' in a radially inward position. Once a desired articulated position of the jaw assembly has been selected, a user can proceed to close and fire the jaw assembly, resulting in distal actuation of the drive beam 26' relative to the elongate shaft. This distal movement of the drive beam 26' advances the ramped and latching segments 362, 364 over the deployment surfaces of the first and second shoes 346, 350, advancing the shoes radially outwardly. (FIG. 43). With the first and second shoes 346, 350 in the radially outward configuration, the first pawl surface 348 engages the first plurality of teeth 342, and the second pawl surface 348 engages the second plurality of teeth 342 to configure the articulation latch mechanism in the latched configuration. Opening the jaw assembly after a firing sequence will reverse the sequence and return the articulation latch to the unlatched configuration. Thus, desirably, actuation of the drive member 26' to close and fire the jaw assembly automatically latches an articulated position of the jaw assembly. Advantageously, this latching can reduce or prevent any tendency of the jaw to 'wag' relative to the elongate shaft as the drive beam is advanced around and retracted through the articulation bend. While the illustrated embodiment of actuation latching mechanism includes meshing arrays of teeth on the shoes and actuation rod and support link that define a plurality of discreet latched positions, it is contemplated that in other embodiments, the shoes, actuation rod, and support link can be configured to frictionally engage to define a continuous array of latched articulation positions. Moreover, while the illustrated embodiment includes two shoes each engageable with a corresponding plurality of teeth, in other embodiments, a single shoe can be advanceable to engage a single plurality of teeth on the articulation rod or support link.

With reference to FIGS. 44 and 45A-45D, a coupler 46 at the distal end of the handle assembly 40 can be coupled to the proximal end of the shaft assembly 20. The coupler 46 can include a bayonet connection with a lock-in. In the illustrated embodiment, the reload shaft 20 to handle 40 connection comprises a bayonet style connection, in which a user axially aligns and inserts the reload shaft 20 into the handle 40 and rotates the reload shaft 20 approximately 90 degrees to connect. This bayonet connection operatively couples two mechanical functions of the reload shaft 20 to corresponding actuators of the handle 40. When the bayonet connection is fully coupled, an articulation member within the shaft 20 is coupled to an articulation adapter of the handle and a drive member within the shaft 20 is coupled to the actuation adapter. Furthermore, the handle 40 and shaft 20 can be configured with a latch mechanism at the coupler 46 to prevent a user from removing the shaft 20 once the actuation adapter and drive member has been activated. Moreover, the connection at the coupler 46 can include a reload identifying mechanism such that the control system of the handle can detect if a reload shaft is connected, and if so what the attached jaw length of the reload is. It is contemplated that the handle can be used with reload shafts 20 including different length jaw assemblies. In some embodiments the same handle 40 can be used with either 45 mm or 60 mm length jaw assemblies.

Figure 45A:
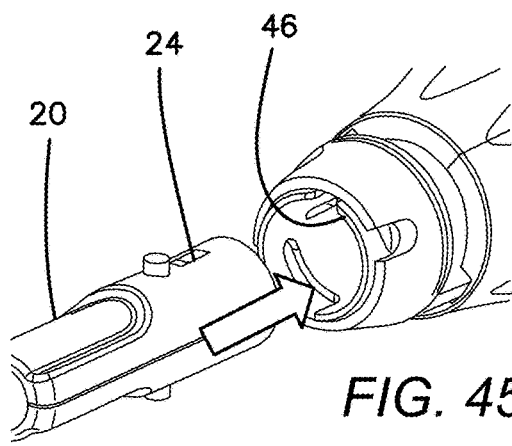
FIGS. 45A-45D are perspective views of a coupling of the proximal end of the shaft assembly to the handle assembly in a stapler system of FIG. 1.

In FIG. 45A, the shaft 20 is positioned in alignment with the coupler 46 on the handle, and a release knob of the coupler 46 is withdrawn to expose a bayonet channel 152 of the coupler 46 on a rotation insert of the coupler 46. The shaft 20 can include a retention post 22 or boss positionable within the bayonet channel 152. In the illustrated embodiment, the shaft includes two bosses positioned 180 degrees apart on the outer surface thereof and the coupler 46 includes a corresponding two bayonet channels 152. It is contemplated that in other embodiments, other numbers and configurations of bosses and bayonet channels can be used to provide a desired connection strength and ease of alignment.

Figure 45B:
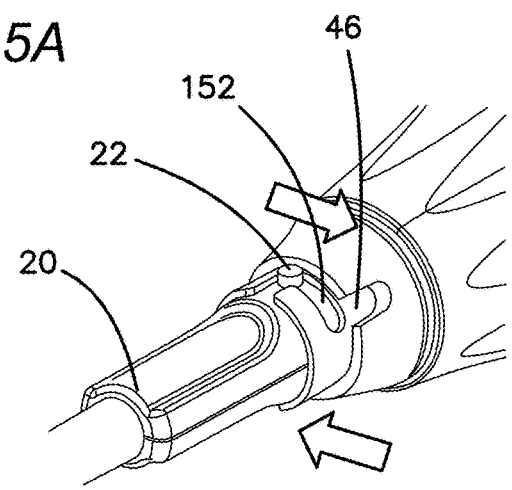
Figure 45C:
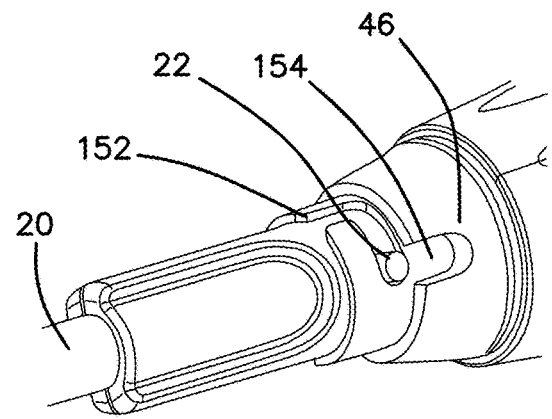
Figure 45D:
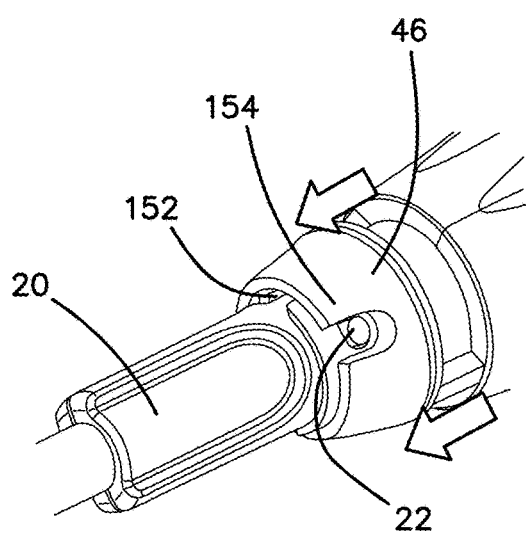

With reference to FIG. 45B, the retention post 22 of the shaft is positioned within the bayonet channel 152. With reference to FIG. 45C, the reload shaft 20 has been rotated 90 degrees relative to the handle such that the retention post 22 of the shaft has reached a connected end of the bayonet channel 152. With reference to FIG. 45D, the release knob of the coupler is released to allow a retention recess 154 on the release knob to retain the retention post 22 of the reload shaft 20.

Figure 46:
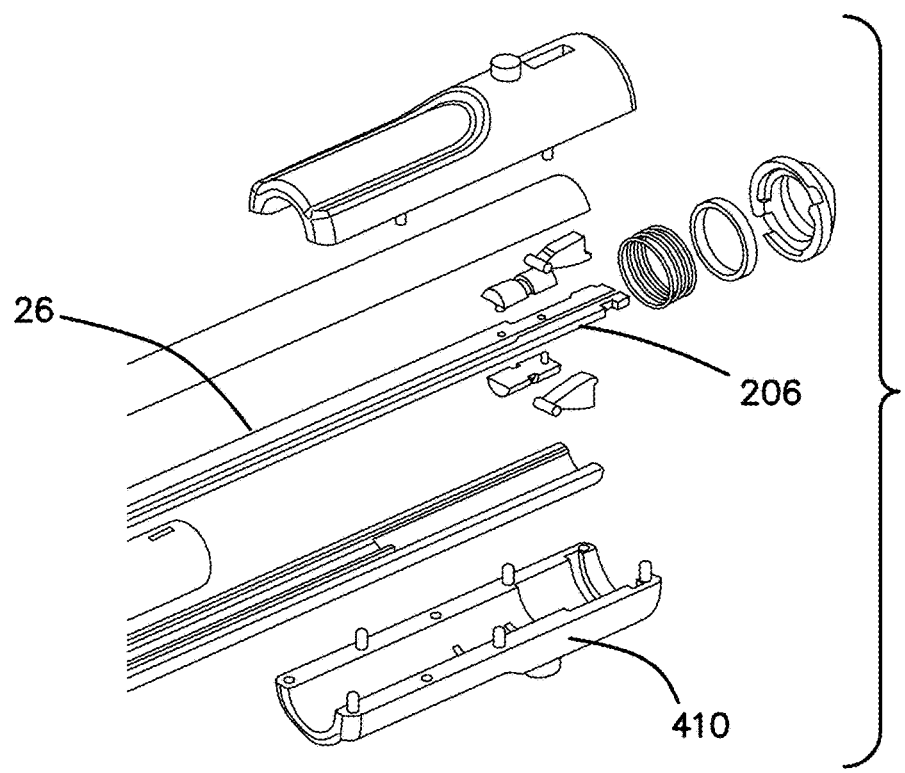
FIG. 46 is an exploded perspective view of the proximal end of the shaft assembly of the stapler system of FIG. 1.
Figure 47:
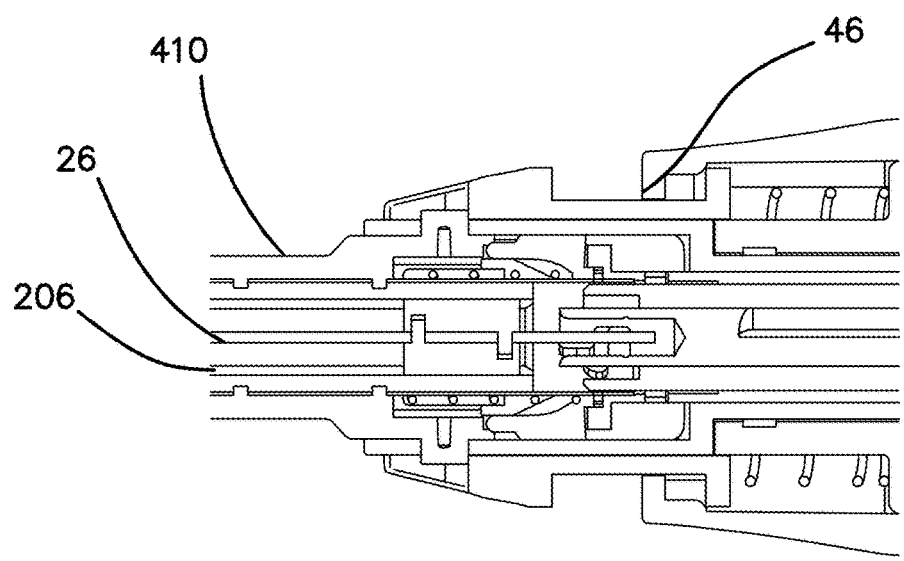
FIG. 47 is a cut-away side view of the proximal end of the shaft assembly positioned adjacent a handle assembly for the stapler system of FIG. 1.

With reference to FIGS. 46 and 47, the shaft assembly can include a tubular shaft with the drive member or drive beam 26 and articulation member 206 extending therethrough from the proximal end to the distal end. The drive member can extend generally centrally through the shaft assembly while the articulation member is laterally offset. The proximal end of the tubular shaft can include a coupling collar 410 for coupling to the coupler 46 at the distal end of the handle. In the illustrated embodiment, the shaft assembly can include a proximal shaft 'lock out' mechanism. The lockout mechanism comprises a locking ring positioned within a shaft coupler at the proximal end of the elongate shaft and at least one lockout member radially outwardly advanceable through the coupling collar 410. The lockout member can be biased radially outwardly, but held in a radially inward position by the locking ring in an initial position. When the proximal end of the shaft is coupled to a handle assembly in a rotation sequence corresponding to a bayonet connection, the locking ring is engaged with a mating surface in the handle assembly and rotates relative to the elongate shaft. This rotation of the locking ring releases the lockout member. Upon removal of the shaft from the handle assembly, the lockout member radially expands. In this expanded position, the lockout member interferes with recoupling the elongate shaft to the handle assembly. Thus, this lockout mechanism can serve to limit inadvertent reuse of an elongate shaft assembly.

Figure 48A:
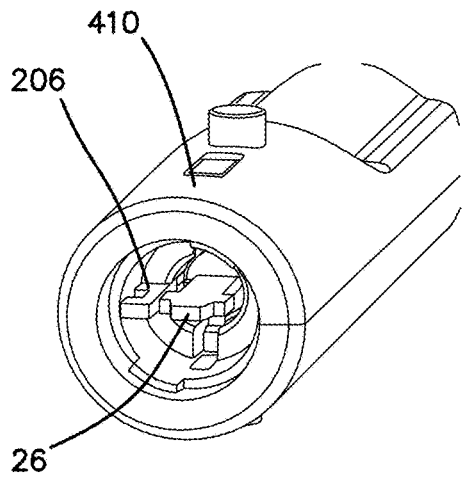
FIGS. 48A-48B are perspective views of a coupling of the proximal end of the shaft assembly to the handle assembly in a stapler system of FIG. 1.
Figure 48B:
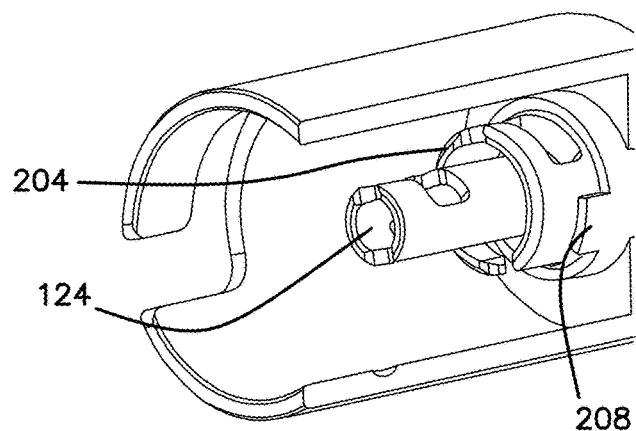
Figure 49A:
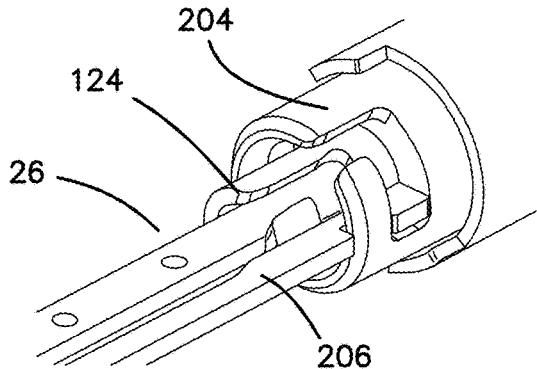
FIGS. 49A-49B are perspective partial cut-away views of a coupling of the proximal end of the shaft assembly to the handle assembly in a stapler system of FIG. 1.
Figure 49B:
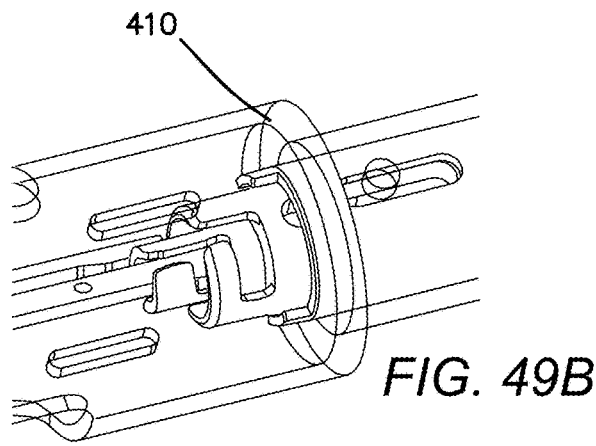

With reference to FIGS. 48A and 48B, engagement of the bayonet coupling between the shaft assembly and the handle is illustrated. The coupler of the handle can comprise a rotation sleeve for coupling to the coupling collar 410 in which an actuation adapter 124, an articulation adapter 204, and an identification sleeve 208 are positioned. During a bayonet coupling, the drive member of the shaft engages 26 with the actuation adapter 124, the articulation member 206 of the shaft engages with the articulation adapter 204, and a shaft identifier engages with the identification sleeve 208. FIGS. 49A and 49B illustrate the respective engagements with the shaft in a coupled configuration.

Figure 50:
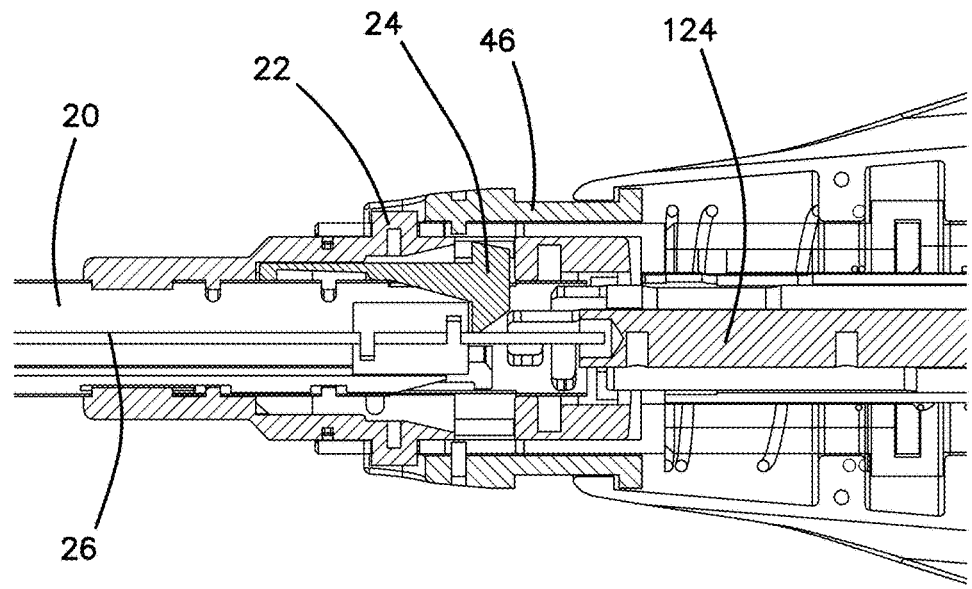
FIG. 50 is a perspective partial cut-away view of the proximal end of the shaft assembly in a stapler system of FIG. 1.
Figure 51:
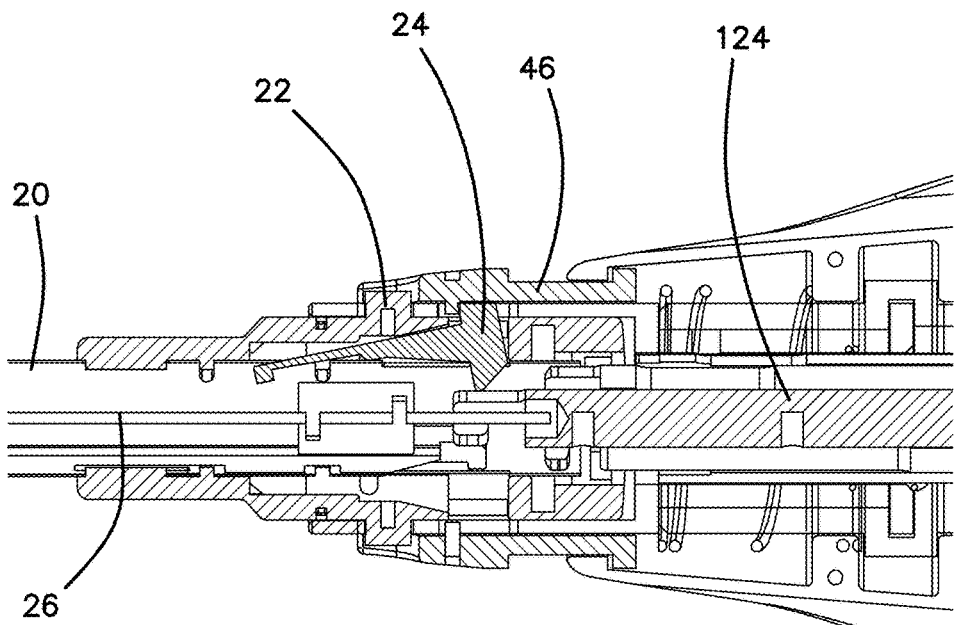
FIG. 51 is a perspective partial cut-away view of the proximal end of the shaft assembly in a stapler system of FIG. 1.

With reference to FIGS. 50 and 51, instead of or in addition to the lockout mechanism described with reference to FIGS. 46 and 47, certain embodiments of elongate shaft can include a lock-in or retention mechanism that operates upon initial distal advancement of the actuation adapter 124. As illustrated, a locking member 24 is pivotably coupled to a proximal end of the shaft 20. The locking member 24 can include a ramped or tapered lock surface at a proximal edge thereof. As illustrated in FIG. 50, the shaft 20 is in a coupled, but unlocked configuration with respect to the coupler 46. In the coupled, unlocked configuration, the shaft 20 can be removed from the coupler 46 through the bayonet connection by a reverse of the sequence of operations of FIGS. 45A-45D. Once the actuation adapter 124 is advancing to operate the stapler, the actuation adapter 124 interacts with the ramped surface of the locking member 24 to advance the locking member radially outward into a locked position. In the locked position (FIG. 51), the locking member 24 engages a locking ledge on the coupler 46 to lock in the shaft. With the shaft 20 locked in with respect to the handle 40, the shaft 20 cannot be removed from the handle 40 until the actuation adapter 124 has been returned to a fully proximally retracted position (typically corresponding to a return to a jaws open configuration following a full closure and stapling cycle of the jaw assembly).

Thus, the "lock In" feature prevents a user from removing the shaft from the handle once the drive member 26 has been driven forward. Once the locking member 24 is situated in the slot or ledge of a rotation insert of the coupler 46, a release knob of the coupler 46 is restricted from being pulled back. This locking action on the coupler prevents the user from rotating the shaft 20 out of the bayonet connection of the coupler 46.

Figure 52:
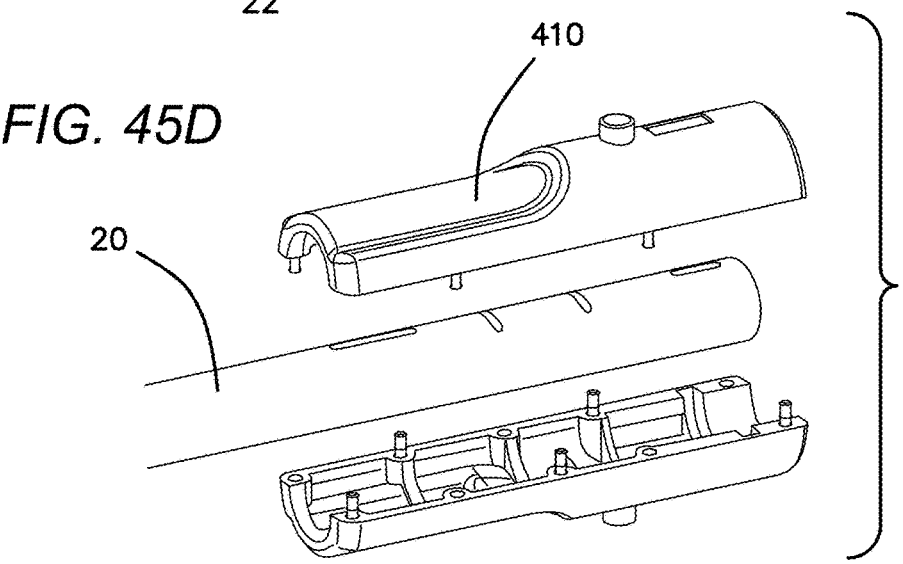
FIG. 52 is an exploded perspective view of the proximal end of the shaft assembly in a stapler system of FIG. 1.

With reference to FIG. 52, a proximal end of the shaft assembly comprises a shaft coupler or coupling collar 410 positioned on the proximal end of the tubular shaft. Thus, the stapling system described herein can easily be adapted for use with shaft assemblies having various diameters. In some embodiments, an inner diameter the shaft coupler can be readily resized to accommodate various tubular shafts without requiring different handle assemblies to accommodate shaft assemblies of various diameters.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims.

What is claimed is:

1. A reload assembly for a surgical stapling system, the reload assembly comprising:
    an elongate shaft having a proximal end and a distal end and defining a longitudinal axis extending between the proximal end and the distal end;
    a jaw assembly positioned at the distal end of the elongate shaft, the jaw assembly comprising:
        a first jaw comprising a reload support configured to receive a staple reload; and
        a second jaw pivotably coupled to the first jaw, the second jaw comprising an anvil surface;
    a firing member longitudinally slidable within the jaw assembly from a proximal position in which the jaw assembly is open to a distal position, the firing member having a tail portion extending proximally therefrom;
    an actuation beam longitudinally slidable within the elongate shaft, the actuation beam having a proximal end and a distal end, the distal end of the actuation beam coupled to the firing member, wherein the actuation beam comprises a lock recess formed therein; and
    a reload lockout mechanism comprising:
        a lockout lever having a proximal end and a distal end, the lockout lever pivotally coupled to the reload support and pivotable between a locked position preventing distal movement of the actuation beam relative to the elongate shaft and an unlocked position allowing distal movement of the actuation beam relative to the elongate shaft, and wherein the tail portion of the firing member engages the proximal end of the lockout lever to maintain the lockout lever in the unlocked position with the firing member in the proximal position and with no staple reload inserted in the reload support.

2. The reload assembly of claim 1, wherein the lockout lever comprises a pivot between the proximal end and the distal end, the pivot defining a pivot axis of the lockout lever.

3. The reload assembly of claim 2, wherein the pivot axis is perpendicular to the longitudinal axis of the elongate shaft.

4. The reload assembly of claim 1, wherein the lockout lever engages the lock recess when the lockout lever is in the locked position.

5. The reload assembly of claim 1, wherein with no staple reload inserted in the reload support, the lockout lever pivots from the unlocked position to the locked position as the firing member is advanced distally from the proximal position.

6. The reload assembly of claim 1, wherein with the lockout lever in the locked position, the proximal end of the lockout lever interferes with the lock recess on the actuation beam.

7. A reload assembly for a surgical stapling system, the reload assembly comprising:
    an elongate shaft having a proximal end and a distal end and defining a longitudinal axis extending between the proximal end and the distal end;
    a jaw assembly positioned at the distal end of the elongate shaft, the jaw assembly comprising:
        a first jaw comprising a reload support configured to receive a staple reload; and
        a second jaw pivotably coupled to the first jaw, the second jaw comprising an anvil surface;
    a firing member longitudinally slidable within the jaw assembly from a proximal position in which the jaw assembly is open to a distal position, the firing member having a tail portion extending proximally therefrom;
    an actuation beam longitudinally slidable within the elongate shaft, the actuation beam having a proximal end and a distal end, the distal end of the actuation beam coupled to the firing member, wherein the actuation beam comprises a lock recess formed therein;
    a reload lockout mechanism comprising:
        a lockout lever having a proximal end and a distal end, the lockout lever pivotally coupled to the reload support and pivotable between a locked position preventing distal movement of the actuation beam relative to the elongate shaft and an unlocked position allowing distal movement of the actuation beam relative to the elongate shaft, and wherein the tail portion of the firing member engages the proximal end of the lockout lever to maintain the lockout lever in the unlocked position with the firing member in the proximal position and with no staple reload inserted in the reload support; and a staple reload positionable in the reload support, the reload comprising:
- a plurality of staples positioned therein, and
- a slider longitudinally advanceable within the reload from a proximal position to a distal position to deploy the staples from the reload, the slider comprising a slider tail extending proximally therefrom;
- wherein the slider tail engages the lockout lever with the slider in the proximal position to maintain the lockout lever in the unlocked position.

8. The reload assembly of claim 7, wherein the slider tail acts on a lower surface of a distal portion of the lockout lever.

9. The reload assembly of claim 7, wherein the staple reload comprises retention tabs and the reload support comprises recesses therein to receive the retention tabs to prevent distal movement of the staple reload relative to the reload support.

10. The reload assembly of claim 7, wherein the staple reload comprises upwardly protruding bosses positioned at a proximal end thereof, the protruding bosses defining a gap between the anvil surface and the staple reload with the jaw assembly in a closed configuration.

* * * * *